United States Patent
Gregersen et al.

(10) Patent No.: US 9,426,989 B2
(45) Date of Patent: Aug. 30, 2016

(54) ORGANIC PEROXIDE COMPOUNDS FOR MICROORGANISM INACTIVATION

(75) Inventors: Jens Peter Gregersen, Marburg (DE); Thomas Grundemann, Berlin (DE)

(73) Assignee: NOVARTIS AG, Basel (CH)

( * ) Notice: Subject to any disclaimer, the term of this patent is extended or adjusted under 35 U.S.C. 154(b) by 778 days.

(21) Appl. No.: 13/696,595

(22) PCT Filed: May 6, 2011

(86) PCT No.: PCT/IB2011/001394
§ 371 (c)(1),
(2), (4) Date: Feb. 19, 2013

(87) PCT Pub. No.: WO2011/138682
PCT Pub. Date: Nov. 10, 2011

(65) Prior Publication Data
US 2013/0149194 A1      Jun. 13, 2013

Related U.S. Application Data

(60) Provisional application No. 61/395,117, filed on May 6, 2010.

(51) Int. Cl.

| | |
|---|---|
| C12N 7/06 | (2006.01) |
| C12N 1/36 | (2006.01) |
| A01N 31/02 | (2006.01) |
| A01N 35/02 | (2006.01) |
| A01N 43/24 | (2006.01) |
| C12N 7/00 | (2006.01) |
| A61K 39/00 | (2006.01) |

(52) U.S. Cl.
CPC ............... *A01N 31/02* (2013.01); *A01N 35/02* (2013.01); *A01N 43/24* (2013.01); *C12N 7/00* (2013.01); *A61K 39/00* (2013.01); *C12N 2720/12063* (2013.01); *C12N 2760/16063* (2013.01); *C12N 2760/16163* (2013.01)

(58) Field of Classification Search
CPC ....... C12N 7/06; A01N 31/02; C07C 409/04
See application file for complete search history.

(56) References Cited

U.S. PATENT DOCUMENTS

| | | | |
|---|---|---|---|
| 3,560,395 A | 2/1971 | Westbrook et al. | |
| 4,060,644 A * | 11/1977 | Braid | A23B 4/24 426/261 |
| 5,489,434 A | 2/1996 | Oakes et al. | |
| 5,627,276 A * | 5/1997 | Greer | C12N 1/08 435/135 |
| 5,824,536 A * | 10/1998 | Webster | A61K 39/145 435/235.1 |
| 2002/0107288 A1 | 8/2002 | Singh et al. | |
| 2003/0012804 A1 | 1/2003 | Cutler et al. | |
| 2004/0219662 A1 * | 11/2004 | Geiger | A61L 2/0088 435/287.1 |
| 2004/0253272 A1 * | 12/2004 | Kaneda | A61K 35/76 424/204.1 |
| 2005/0118940 A1 | 6/2005 | Hilgren et al. | |
| 2007/0031451 A1 * | 2/2007 | Slifka | A61K 33/40 424/204.1 |
| 2007/0112062 A1 | 5/2007 | Luengo et al. | |
| 2008/0262097 A1 | 10/2008 | Eady et al. | |
| 2009/0030086 A1 | 1/2009 | Eady et al. | |
| 2009/0186948 A1 | 7/2009 | Chavez Inzunza | |
| 2009/0304729 A1 | 12/2009 | Gregersen et al. | |

FOREIGN PATENT DOCUMENTS

| | | |
|---|---|---|
| CN | 1436787 | 8/2003 |
| CN | 101203205 | 6/2008 |
| CN | 101365480 | 2/2009 |
| DE | 19817743 | 10/1999 |
| EP | 0024304 | 3/1981 |
| EP | 0228137 | 7/1987 |
| EP | 0461700 | 12/1991 |
| EP | 0985349 | 3/2000 |
| GB | 998686 | 7/1965 |
| JP | 8-502415 | 3/1996 |
| JP | 2004-091332 | 3/2004 |
| WO | WO 9410289 | 5/1994 |
| WO | WO 9707708 | 12/1997 |
| WO | WO 2006100495 | 9/2006 |
| WO | WO 2007042175 | 4/2007 |

OTHER PUBLICATIONS

Shoeb et al., "Antimicrobial Activity of Artemisinin and Its Derivatives Against Anaerobic Bacteria", Journal of Chemotherapy,2(6):362-367 (1990) ISSN: 1120-0009X.
Todorovic et al., "Steroidal Geminal Dihydroperoxides and 1, 2, 4, 5-Tetraoxanes: Structure Determination and Their Antimalarial Activity", Steroids, Elsevier Science Publishers, New York, NY, US, 61(12):688-696 (1996) XP004016628, ISSN:0039-128X, DOI: 10.1016/S0039-128X(96)00203-6.
Technology Transfer Network Air Toxins, Technical information on beta-propiolactone from E.P.A. ("Uses" paragraph) (2007)—D15.
Notice of Reasons for Rejection dated Feb. 16, 2016, which issued during prosecution of Japanese Application No. 2013-508577.
Hamann, et al. "Reaction of Epoxyketones with Hydrogen Peroxide-Ethane-1,1-dihydroperoxide as a Surprisingly Stable Product" Chemistry, 2008, 14(23):6849-6851.
Shkidchenko, et al. "Bactericidal action of β-propiolactone homologue" Process Biochemistry, 2004, 39 (11):1465-1468.

\* cited by examiner

*Primary Examiner* — Sean E Conley
*Assistant Examiner* — Donald Spamer
(74) *Attorney, Agent, or Firm* — Vedder Price P.C.; Thomas J. Kowalski; Mark W. Russell

(57) ABSTRACT

Multifunctional organic peroxides are used as microbiological inactivators and/or for degrading nucleic acids. These include at least one carbon atom and at least two organic peroxide groups. The inactivator is ideally a hydroperoxide. The invention is particularly useful during preparation of viral vaccines.

35 Claims, 3 Drawing Sheets

ORGANIC PEROXIDE COMPOUNDS FOR MICROORGANISM INACTIVATION

CROSS REFERENCE TO RELATED APPLICATIONS

This application is a U.S. National Phase patent application of PCT/IB2011/001394, filed May 6, 2011, which claims priority to U.S. Provisional patent application Ser. No. 61/395,117 filed, May 6, 2010, all of which are hereby incorporated by reference in the present disclosure in their entirety.

TECHNICAL FIELD

The invention is in the field of compounds which are useful for inactivating microorganisms and/or for degrading nucleic acids (and in particular, for degrading DNA).

BACKGROUND ART

Treatment of viruses and bacteria to render them inactive is important in various areas, including sanitisation of waste water or sewage, and also in the field of parenteral medicines such as vaccines. For instance, many vaccines are based on microorganisms which are inactivated to ensure that live infectious material is absent from the final vaccine. Failure of inactivation can present severe safety risks, as known from "the Cutter incident" in the 1950s where inactivation of poliovirus failed.

Inactivation treatments are typically based on chemical means. Chemical treatments include the use of detergents, formaldehyde (usually as formalin), β-propiolactone (BPL), glutaraldehyde, ethyleneimines, phenol etc. These inactivators have been used for many years e.g. see reference 1.

Some of these inactivators are also useful for degrading nucleic acids. This degradation can play a role in inactivating the viruses or bacteria themselves, but it can also be useful for eliminating residual nucleic acids from any cell substrate which has been used during growth. For example, viruses can be grown in cell culture to provide material for preparing vaccines and during manufacture it is usual to include a step to degrade any residual nucleic acids from the cell culture substrate, thereby removing potentially oncogenic material. Reference 2 describes the use of BPL for both inactivating viruses and degrading host cell DNA.

The best inactivator varies according to the particular microorganism. For instance, differences in viral morphology (size, capsidation, envelope, etc.) lead to differences in inactivation sensitivity e.g. see Appendix 2 of reference 3. Although some treatments are universally able to inactivate microorganisms (e.g. very harsh heat, disinfecting agents, strong UV light or radiation), these also destroy immunogenicity and so are inappropriate for preparing effective vaccines. Inactivation treatments are instead chosen so that they are effective for the microorganism in question while retaining vaccine immunogenicity. Unfortunately, the treatment may thus leave contaminating agents in an active form, possibly leading to vaccine contamination by hardy infectious agents. There is thus a need for broad-spectrum inactivators which will inactivate both target microorganisms and potential contaminants. Such inactivators would also be useful for treating products such as bovine serum or trypsin, where viral inactivation is recommended [4].

Another difficulty with some inactivators is their stability. Formaldehyde is an effective inactivator, particularly at high temperatures, but it is very stable and so residues remain after inactivation. These residues can interfere with downstream testing for residual active microorganisms. Thus high dilutions are used in these tests, but this reduces their sensitivity. Moreover, the residues can interfere with immune responses in final vaccines e.g. ref. 5 suggests that formalin-inactivated vaccines might have a higher risk of causing hypersensitivity.

Finally, inactivation with formaldehyde can be reversible in some circumstances [6,7].

There is thus a need for new and improved microorganism inactivators. These should be useful against a variety of microorganisms, including hardy ones, without removing desired immunogenicity. They should also leave little or no interfering or harmful residues, and the inactivation should not be reversible. Ideally, they should also be suitable for degrading nucleic acid, and should display their activity even in the presence of aqueous media.

DISCLOSURE OF THE INVENTION

The invention uses multifunctional organic peroxides as microbiological inactivators and/or for degrading nucleic acids. These inactivators include (i) at least one carbon atom or backbone and (ii) at least two peroxide groups i.e. at least two groups which contain a single bond between two oxygen atoms —O—O—. The inactivator is ideally a hydroperoxide i.e. containing the group —O—O—H. Such compounds are already known in the art, but they are now shown to be potent inactivators of microorganisms, including for notoriously stable viruses such as reovirus, which can achieve inactivation without negatively affecting immunogenicity. Moreover, they can be highly water soluble, produce no toxic degradation products (e.g. producing only simple carboxylic acids such as acetic, propionic, or butyric acids, etc.), and are active over a wide range of pH and temperatures. Furthermore, they can show surprising stability in aqueous conditions, and they are effective to degrade cellular DNA.

Thus the invention provides a process for treating a microorganism-containing sample (such as a liquid sample), comprising contacting the sample with a multifunctional organic peroxide. This process can result in inactivation of the microorganisms within the sample.

The invention also provides a process for treating a sample (such as a liquid sample) which contains nucleic acids (such as DNA e.g. cellular DNA), comprising contacting the sample with a multifunctional organic peroxide. This process can result in degradation of nucleic acid within the sample.

The invention also provides a method for preparing a pharmaceutical composition, comprising steps of: (i) contacting a microorganism-containing sample with a multifunctional organic peroxide to inactivate microorganisms therein; (ii) preparing the pharmaceutical composition from the product of step (i). This pharmaceutical composition is usefully a vaccine, such as a viral vaccine.

The invention also provides a pharmaceutical composition, comprising (i) an active agent, such as a viral immunogen, and (ii) the reaction product of a multifunctional organic peroxide and a reducing agent. The reducing agent and the reaction product should be non-toxic e.g. both might be sugars.

The invention also provides an aqueous solution of a multifunctional organic peroxide, wherein the multifunctional organic peroxide is present at a concentration of either (a) less than 1% by weight or (b) between 5-70% by weight. This solution, particularly in option (a), may also contain microorganisms. In option (a) the concentration is usually in the range 0.001-0.5% e.g. between 0.01-0.25%, between 0.01-0.1, or about 0.05%. In option (b) the concentration can be in the range 6-60%, 7-50%, 8-40%, 9-35% or 10-30%.

The invention also provides a liquid composition comprising (i) inactivated microorganisms and (ii) less than 1% by weight (for example, in the range 0.001-0.5% e.g. between 0.01-0.25%, between 0.01-0.1, or about 0.05%) of a multifunctional organic peroxide.

The invention also provides a liquid composition comprising the reaction product of a microorganism and a multifunctional organic peroxide.

The invention also provides a disinfectant composition comprising a multifunctional organic peroxide. Such solutions include the aqueous solutions discussed above, but absent microorganisms.

The invention also provides any of the above compositions, for use in the manufacture of a medicament e.g. for use in the manufacture of a vaccine. Similarly, the invention provides a process for manufacturing a medicament, in which the process uses any of the above compositions.

The invention also provides the use of a multifunctional organic peroxide as a microbiological inactivator. The invention also provides a multifunctional organic peroxide for use as a microbiological inactivator. The invention also provides the use of an aqueous solution of the invention as a microbiological inactivator. The invention also provides an aqueous solution of the invention for use as a microbiological inactivator.

The Sample

The invention is useful for treating a microorganism-containing samples. These samples are preferably liquid samples, but could also be solid e.g. the surface of a container or workplace. Such samples include, but are not limited to: microbial culture fluids; blood products, serum, plasma, or blood-derived preparations (e.g. anti-coagulants); animal-derived raw materials and products; other raw materials which may be contaminated by microorganisms; recombinant proteins, materials and intermediates in vaccines and diagnostics production (e.g. ELISAs); waste materials from processes utilizing microbial agents; waste water, sewage; foodstuffs (e.g. milk); etc.

The invention has a further use in disinfection or sterilisation of samples, and in particular for disinfection of surfaces to destroy microorganisms that are living on them. For example, the invention can be used for disinfecting a work surface prior to use, for sterilising surgical instruments or implants prior to use, or for any other purpose in which disinfection or sterilisation is desirable.

The invention is useful for inactivating various types of microorganism, including both viruses and bacteria. It can be used with enveloped viruses and non-enveloped viruses. It can be used with viruses having a RNA genome (single- or double-stranded) or a DNA genome (single- or double-stranded), and a single-stranded genome may be + or − sense. It can be used with viruses having a segmented genome or a non-segmented genome. It can be used with viruses having a capsid (single or multiple) or viruses having no capsid. It can be used with Gram-negative bacteria or Gram-positive bacteria.

Thus the sample may contain one or more of the following:

Orthomyxovirus: The invention may be used to inactive an orthomyxovirus, such as an influenza A, B or C virus. Influenza A or B viruses may be interpandemic (annual/seasonal) strains, or from strains with the potential to cause a pandemic outbreak (i.e., influenza strains with new hemagglutinin compared to a hemagglutinin in currently circulating strains, or influenza strains which are pathogenic in avian subjects and have the potential to be transmitted horizontally in the human population, or influenza strains which are pathogenic to humans). Depending on the particular season and on the nature of the strain, an influenza A virus may be derived from one or more of the following hemagglutinin subtypes: H1, H2, H3, H4, H5, H6, H7, H8, H9, H10, H11, H12, H13, H14, H15 or H16.

Paramyxoviridae viruses: The invention may be used to inactive Paramyxoviridae viruses, such as Pneumoviruses (RSV), Paramyxoviruses (PIV) and Morbilliviruses (Measles).

Pneumovirus: The invention may be used to inactive a Pneumovirus or a metapneumovirus, for example respiratory syncytial virus (RSV), Bovine respiratory syncytial virus, Pneumonia virus of mice, and Turkey rhinotracheitis virus. Preferably, the Pneumovirus is RSV or human metapneumovirus (HMPV).

Paramyxovirus: The invention may be used to inactive a Paramyxovirus, such as Parainfluenza virus (PIV) type 1, 2, 3 or 4, Mumps, Sendai viruses, Simian virus 5, Bovine parainfluenza virus and Newcastle disease virus. Preferably, the Paramyxovirus is PIV or Mumps.

Morbillivirus: The invention may be used to inactive a Morbillivirus, such as Measles.

Picornavirus: The invention may be used to inactive Picornaviruses, such as Enteroviruses, Rhinoviruses, Heparnavirus, Cardioviruses and Aphthoviruses.

Enterovirus: The invention may be used to inactive an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus e.g. a type 1 strain such as Mahoney or Brunenders, a type 2 strain such as MEF-I, or a type 3 strain such as Saukett.

Heparnavirus: The invention may be used to inactive an Heparnavirus (also named Hepatovirus), such as Hepatitis A virus.

Togavirus: The invention may be used to inactive a Togavirus, such as a Rubivirus, an Alphavirus, or an Arterivirus. Rubiviruses, such as Rubella virus, are preferred. Useful alphaviruses for inactivation include aquatic alphaviruses, such as salmon pancreas disease virus and sleeping disease virus.

Flavivirus: The invention may be used to inactive a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis.

Hepatitis C virus: The invention may be used to inactive a Hepatitis C virus (HCV).

Pestivirus: The invention may be used to inactive a Pestivirus, such as Bovine viral diarrhea (BVDV), Classical swine fever (CSFV) or Border disease (BDV).

Hepadnavirus: The invention may be used to inactive a Hepadnavirus, such as Hepatitis B virus.

Rhabdovirus: The invention may be used to inactive a Rhabdovirus, such as a Lyssavirus (e.g. a rabies virus) and Vesiculovirus (VSV).

Caliciviridae; The invention may be used to inactive Calciviridae, such as Norwalk virus, and Norwalk-like Viruses, such as Hawaii Virus and Snow Mountain Virus, and Vesivirus, such as Vesicular Exanthema of Swine Virus.

Coronavirus: The invention may be used to inactive a Coronavirus, such as a SARS, Human respiratory coronavirus, Avian infectious bronchitis (IBV), Mouse hepatitis virus (MHV), and Porcine transmissible gastroenteritis virus (TGEV).

Retrovirus: The invention may be used to inactive a Retrovirus, such as an Oncovirus, a Lentivirus or a Spumavirus. An oncovirus may be HTLV-1, HTLV-2 or HTLV-3. A lentivirus may be SIV, HIV-1 or HIV-2.

Reovirus: The invention may be used to inactive a Reovirus, such as an Orthoreovirus, a Rotavirus, an Orbivirus, or a Coltivirus.

Parvovirus: The invention may be used to inactive a Parvovirus, such as Parvovirus B19, or Bocavirus.

Other hepatitis viruses: The invention may be used to inactive a hepatitis delta virus, a hepatitis E virus, or a hepatitis G virus.

Human Herpesvirus: The invention may be used to inactive a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: The invention may be used to inactive Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65.

Adenoviridae. The invention may be used to inactive adenoviruses, including any of human adenoviruses A, B, C, D, E, F or G.

*Bordetella*: The invention may be used to inactivate *Bordetella* bacteria, such as *B. pertussis*.

Clostridiaceae: The invention may be used to inactivate Clostridia, such as *C. tetani* and *C. botulinum*

Corynebacteriaceae: The invention may be used to inactivate *Corynebacteria*, such as *C. diphtheriae.*

Pasteurellaceae: The invention may be used to inactivate *Pasteurella* species, such as *Haemophilus influenzae*.

Mycobactericeaea: The invention may be used to inactivate *Mycobacteria*, such as *M. tuberculossi, M. bovis* and the attenuated *Bacillus Calmette* Guerin.

Neisseriaceae: The invention may be used to inactivate *Neisseria* species, such as *N. meningitidis* and *N. gonorrhoeae.*

Salmonellaceae: The invention may be used to inactivate *Salmonella* species, such as *S. typhi, S. paratyphi, S. typhimurium, S. enteritidis.*

Steptococcaceae: The invention may be used to inactivate a Streptococci, such as *S. pneumoniae* (pneumococcus), *S. agalactiae* and *S. pyogenes*.

Mycoplasmataceae: The invention may be used to inactivate Mycoplasmas, such as *M. pneumonia, M. hyorhinis, M. bovis, M. agalactiae, M. gallisepticum*, including any M. species that may be found in contaminated cell cultures or cell culture-derived materials.

In addition to a microorganism, a sample can also include nucleic acid in solution e.g. residual cellular DNA. These conditions can arise when, for instance, a lytic virus has been grown in cell culture and a cell-free harvest has been prepared. In such samples, the multifunctional organic peroxide can both inactivate the microorganism and degrade the nucleic acid in solution, thus offering a double benefit during vaccine manufacture, and in particular for viral vaccines.

Thus a sample for treatment by the invention may comprise a microorganism and cellular DNA (e.g. genomic DNA from a cell line, such as MDCK).

Where a sample includes nucleic acids (with or without also including microorganisms), the nucleic acid typically comprises DNA e.g. cellular DNA. Rather than being nucleic acid inside a microorganism (e.g. inside a bacterium, or inside a virion), the nucleic acid will generally be free in solution e.g. cellular DNA which is in solution, rather than cellular DNA inside a cell (i.e. DNA which is cellular in origin, but which is no longer present inside a cell).

The microorganism may be present intentionally (e.g. after growing virus to prepare a vaccine) or as a contaminant (e.g. in sewage, or after recombinant protein expression, from contaminated cell culture media components, cells or cultures). Also, in some embodiments a sample may deliberately contain a microorganism but may also contain contaminant microorganism(s).

The invention is particularly useful for inactivating viruses, and so a process for treating a microorganism-containing sample is preferably a process for inactivating viruses in a virus-containing sample.

In some embodiments, the invention can be used for treating a sample which is not necessarily microorganism-containing but which is suspected of, or is at risk of, being microorganism-containing. In these embodiments the treatment is not necessary but is used to ensure microorganism inactivation for the avoidance of risk (e.g. in disinfection). In general, the sample will be capable of supporting microorganism growth or persistence.

In addition to including microorganisms a sample may contain other materials e.g. cell substrates or their residues, cellular nucleic acids (e.g. DNA), egg proteins, etc. In addition to inactivating microorganisms, organic peroxides may react with these other materials. Ideally, though, the sample does not include significant amounts of non-infectious materials which compete with the infectious materials for reaction with the inactivators. Such reactions waste the inactivator. Materials which can undergo these futile reactions include, for instance, reducing agents (see below). Thus, for example, a culture which retains a high level of residual glucose could be avoided.

After treatment of the sample according to the invention, remaining or excess peroxide can be removed and/or destroyed. This can be achieved in various ways e.g. by adding a reducing agent. Suitable reducing agents include, but are not limited to, sodium thiosulfate, ascorbic acid, sugars (e.g. glucose or sucrose; preferably reducing sugars), polysaccharides, polyphenols, etc. Reducing agent(s) will typically be added at a molar excess (calculated per reductive group) to the peroxide e.g. at a molar excess of reductive groups to chemical inactivator between 2:1 and 4:1. Reducing agents may be added at sufficient quantities to block the initial concentration of the peroxide. For a well-standardized process with known end-concentration ranges, however, a user may prefer to add a lower concentration e.g. a concentration sufficient to block an amount of peroxide which would remain after inactivation.

Depending on the chemical inactivator and depending on the reducing agent used, the inactivated inactivator can remain in the reaction solution (e.g. if it harmless, such as a simple sugar), or it may be diluted out, or it may be removed. A removal step may take place as part of downstream processing of the reagent of interest (e.g. during purification of a protein or virus component from the inactivated material). Thus removal may involve ultra/diafiltration, dialysis, chromatographic purification, etc.

The Multifunctional Organic Peroxide

The invention uses multifunctional organic peroxides. Such compounds include at least one carbon atom or backbone i.e. they are organic, unlike $H_2O_2$. They also include at least two groups i.e. they contain multiple functional peroxide groups, unlike peracetic acid.

The peroxide compound is ideally a hydroperoxide i.e. containing the group —O—O—H. It may contain multiple hydroperoxide groups. Other multifunctional organic peroxides can be peroxyketals e.g. $CR^1R^2(OOR^3)(OOR^4)$ or tetraoxanes, but compounds including at least one —O—O—H group attached to a carbon atom are preferred.

At least one peroxide group is attached to a carbon atom to give an organic peroxide, and in some embodiments at least one of the oxygen atoms in each peroxide group is attached to a carbon atom.

The peroxide compound is ideally a geminal peroxide (or hydroperoxide), in which two peroxide (or hydroperoxide) groups are attached to the same carbon atom.

The compound ideally has two, three or four peroxide groups, although compounds with a higher number of peroxide groups are not excluded.

The compound can be homobifunctional i.e. it includes two identical peroxide (or hydroperoxide) functional groups; thus an inactivator may be a geminal bishydroperoxide. Alternatively, an inactivator may be heterobifunctional i.e. it includes two different peroxide functional groups e.g. it may include a hydroperoxide (—OOH) and a different peroxide (—OOR, where R≠H).

Preferred compounds are water-soluble. This facilitates their use during vaccine manufacture.

Preferred compounds are halogen-free as such compounds are typically seen as less harmful. Thus an inactivator may consist solely of carbon, hydrogen, oxygen and nitrogen atoms. Particularly preferred compounds consist solely of carbon, hydrogen and oxygen atoms.

Preferred compounds have a molecular weight below 500 e.g. <300, <250, <200, <150, <100.

Preferred compounds do not include a —C(=O)—OOH group and so do not give very acidic pH during inactivation (e.g. unlike peracetic acid). Such conditions can destroy pH-sensitive immunogens, and can also lead to corrosion on the devices and machinery used in the inactivation process.

Preferred compounds are non-explosive e.g. triacetone triperoxide is not preferred.

During inactivation the compound ideally does not form reaction or degradation products which are more toxic to animals (including humans) than the original product.

Preferred compounds can inactivate (i) human influenza A virus with a ≥5, preferably ≥7 log 10 reduction of the infectious titre, and/or (ii) reovirus type 3 with a ≥3, preferably ≥5, and particularly preferred ≥7 log 10 reduction of the infectious titre.

Preferred compounds can inactivate a microorganism without reducing its immunogenicity. Particularly preferred compounds can inactivate influenza A virus without reducing the immunogenicity of its hemagglutinin.

Useful compounds have formula I:

$$R_{1a}\underset{R_{2a}}{\overset{OOH}{\diagup\!\!\!\diagdown}}OOR_3$$

where:

$R_{1a}$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$alkyl, optionally N-mono or N-di $C_{1-6}$alkylated amino, optionally N-mono or N-di $C_{1-6}$alkylated aminocarbonyl, $S(O)_{0-2}C_{1-6}$alkyl, heterocycloalkyl, aryl or heteroaryl;

$R_{2a}$ is H, $C_{1-6}$alkyl, $C_{2-6}$alkenyl, $C_{1-6}$alkynyl, $C_{1-6}$alkoxy, $C_{2-6}$-alkenyloxy, C(O)H, C(O)$C_{1-6}$alkyl, C(O)O$C_{1-6}$ alkyl, optionally N-mono or N-di $C_{1-6}$alkylated amino, optionally N-mono or N-di $C_{1-6}$alkylated aminocarbonyl, $S(O)_{0-2}C_{1-6}$alkyl, heterocycloalkyl, aryl or heteroaryl, —$(CR_4R_5)_nCR_6(OOH)_2$, or $R_{2a}$ is linked to $R_{2b}$ by L;

$R_3$ is H or C(OOH)$R_{1b}R_{2b}$, $R_{1b}$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$ alkyl, optionally N-mono or N-di $C_{1-6}$ alkylated amino, optionally N-mono or N-di $C_{1-6}$alkylated aminocarbonyl, $S(O)_{0-2}C_{1-6}$alkyl, heterocycloalkyl, aryl or heteroaryl, $R_{2b}$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$ alkyl, optionally N-mono or N-di $C_{1-6}$alkylated amino, optionally N-mono or N-di $C_{1-6}$alkylated aminocarbonyl, $S(O)_{0-2}C_{1-6}$alkyl, heterocycloalkyl, aryl or heteroaryl, or $R_{2b}$ is linked to $R_{2a}$ by L;

$R_4$ is, at each occurrence, selected from H or $C_{1-3}$ alkyl, hydroxyl, cyano, nitro, $C_{2-4}$-alkenyl, $C_{1-3}$-alkoxy, $C_{2-4}$-alkenyloxy, $C_{1-3}$-alkylcarbonyl, carboxy, $C_{1-6}$-alkoxycarbonyl, optionally N-mono or N-di $C_{1-3}$alkylated aminocarbonyl, $C_{1-3}$-thioalkyl, $C_{1-3}$-alkylsulfinyl, $C_{1-3}$-alkylsulfonyl, $C_{1-3}$-alkylaminosulfonyl and di-$C_{1-3}$-alkylaminosulfonyl;

$R_5$ is, at each occurrence, selected from H or $C_{1-3}$ alkyl, hydroxyl, cyano, nitro, $C_{2-4}$-alkenyl, $C_{1-3}$-alkoxy, $C_{2-4}$-alkenyloxy, $C_{1-3}$-alkylcarbonyl, carboxy, $C_{1-6}$-alkoxycarbonyl, optionally N-mono or N-di $C_{1-3}$alkylated aminocarbonyl, $C_{1-3}$-thioalkyl, $C_{1-3}$-alkylsulfinyl, $C_{1-3}$-alkylsulfonyl, $C_{1-3}$-alkylaminosulfonyl and di-$C_{1-3}$-alkylaminosulfonyl;

L is $C_{1-8}$alkylene;

$R_6$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$alkyl, optionally N-mono or N-di $C_{1-6}$alkylated amino, optionally N-mono or N-di $C_{1-6}$alkylated aminocarbonyl, $S(O)_{0-2}C_{1-6}$alkyl, heterocycloalkyl, aryl or heteroaryl; and n is 1 to 8.

In addition to these options for $R_{1a}$, $R_{2a}$, $R_3$, $R_{1b}$, $R_{2b}$, $R_4$, $R_5$, and $R_6$, each of these groups can also be a derivative of the listed options.

An alkyl, alkyl moiety of alkoxy radicals, alkenyl, alkenyl moiety of alkenyl radicals, alkynyl or alkylene may be branched or unbranched and/or may be substituted or unsubstituted. Where substituted, each substituent may be selected from: hydroxyl, cyano, nitro, $C_{1-6}$-alkyl, $C_{6-10}$-aryl, benzyl, $C_{2-6}$-alkenyl, $C_{1-6}$-alkoxy, $C_{2-6}$-alkenyloxy, $C_{1-6}$-alkylcarbonyl, carboxy, $C_{1-6}$-alkoxycarbonyl, optionally N-mono or N-di $C_{1-6}$alkylated amino, optionally N-mono or N-di $C_{1-6}$alkylated aminocarbonyl, optionally N-mono or N-di $C_{1-6}$alkylated aminosulfinyl, $C_{1-6}$-thioalkyl, $C_{1-6}$-alkylsulfinyl, $C_{1-6}$-alkylsulfonyl, aminosulfonyl, $C_{1-6}$-alkylaminosulfonyl and di-$C_{1-6}$-alkylaminosulfonyl.

Where $R_3$ is not —H, and $R_{1a}$ is different from $R_{2a}$, these compounds can exist in different enantiomeric forms. The invention can use particular enantiomers or racemic mixtures.

In some embodiments $R_{1a}$ and $R_{2a}$ are identical. In other embodiments $R_{1a}$ and $R_{2a}$ are different.

In some embodiments $R_{1a}$ and $R_{1b}$ are identical. In other embodiments $R_{1a}$ and $R_{1b}$ are different.

In some embodiments $R_{2a}$ and $R_{2b}$ are identical. In other embodiments $R_{2a}$ and $R_{2b}$ are different.

$R_{1a}$ is preferably H or $C_{1-6}$alkyl or $C_{1-4}$allyl. $R_{1a}$ can thus be H or $CH_3$.

$R_{2a}$ is preferably H or $C_{1-6}$alkyl or $C_{1-4}$alkyl or $-(CH_2)_n CH(OOH)_2$ or is linked to $R_{2b}$ by L. $R_{2a}$ can thus be $CH_3$, Et, n-Pr or $-(CH_2)_{2-4}CH(OOH)_2$ $R_{1b}$ is preferably H or $C_{1-6}$alkyl or $C_{1-4}$alkyl or. $R_{1b}$ can thus be H or $CH_3$.

$R_{2b}$ is preferably $C_{1-4}$alkyl or is linked to $R_{2a}$ by L. $R_{2b}$ can thus be $CH_3$, Et, or n-Pr.

Each $R_4$ (which may be the same or different) is preferably H or $-CH_3$ or hydroxyl.

Each $R_5$ (which may be the same or different) is preferably H or $-CH_3$ or hydroxyl.

L is preferably $C_{2-5}$alkylene, such as $-(CH_2)_3-$.

$R_6$ is preferably H or $C_{1-6}$alkyl or $C_{1-4}$alkyl.

n is preferably 2 to 6, or is 2 to 4, or is 3.

In one embodiment: $R_{1a}$ is H or $CH_3$; $R_{2a}$ is $CH_3$, Et, n-Pr, or $-(CH_2)_n CH(OOH)_2$, or $R_{2a}$ is linked to $R_{2b}$ by L; $R_3$ is H or $C(OOH)R_{1b}R_{2b}$; $R_{1b}$ is H or $CH_3$; $R_{2b}$ is $CH_3$, Et, or n-Pr, or $R_{2b}$ is linked to $R_{2a}$ by L; L is $-(CH_2)_3-$; and n is 3.

The compound may have formula II:

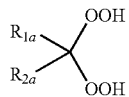

where, in preferred embodiments: $R_{1a}$ is H or $CH_3$; and $R_{2a}$ is $CH_3$, Et, or n-Pr.

The compound may have formula III:

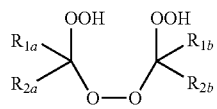

where, in preferred embodiments: $R_{1a}$ is H or $CH_3$; $R_{2a}$ is $CH_3$, Et, or n-Pr, or $R_{2a}$ is linked to $R_{2b}$ by L; $R_{1b}$ is H or $CH_3$; $R_{2b}$ is $CH_3$, Et, n-Pr, or $R_{2b}$ is linked to $R_{2a}$ by L; and L is $-(CH_2)_3-$.

The compound may have formula IV:

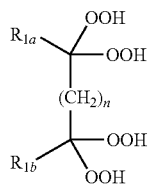

where, in preferred embodiments: $R_{1a}$ is H; $R_{1b}$ is H; and n is 3.

Suitable compounds include, but are not limited to: 2,2'-Dihydroperoxy-2,2'-dibutylperoxide; 2,2-Dihydroperoxybutane; 1,1-Dihydroperoxyethane; 1,1-Dihydroperoxypropane; 1,1-Dihydroperoxybutane; 1,1'-Dihydroperoxy-1,1'-dipropylperoxide; 1,1'-Dihydroperoxy-1,1'-dibutylperoxide; 1,1'-Dihydroperoxy-1,1'-diethylperoxide; 1,1,5,5-Tetrahydroperoxypentane; 3,7-Bis-hydroperoxy-1,2-dioxepane; and 1,1-Dihydroperoxymethane. 1,1-dihydroperoxyethane is preferred. At least some of these compounds are already known in the art (e.g. see references 8-10) and/or are available from commercial suppliers e.g. from Ferak AG (Berlin, DE) or from Arkema Inc. (Philadelphia, US). Compounds from references 8-10 or available from these suppliers, and particularly their water-soluble compounds, can be used with the invention.

The invention may use a single inactivator compound or a mixture of compounds e.g. comprising more than one different compound of formula I. Where a mixture includes two different organic peroxides, these may be present at various molar ratios e.g. between 10:1 and 1:10, between 5:1 and 1:5, between 2:1 and 1:2, or at a substantially equimolar ratio. Compounds in a mixture may show hydrogen bonding to form cyclic structures e.g. between molecules of 056-1 and 058-1. Some compounds may exist as dimers, and may also exist as mixtures of monomers and oligomers.

Thus the invention can use a mixture comprising a compound of formula II and a compound of formula III. In such mixtures: $R_{1a}$ and $R_{1b}$ can be the same in both formula II and formula III; and/or $R_{2a}$ and $R_{2b}$ can be the same in both formula II and formula III.

Inactivators are used at a concentration sufficient to inactivate microorganisms in the sample of interest, ideally without reducing the immunogenicity of a desired microorganism (or its components). They will generally be mixed with a liquid sample to give a final concentration of less than 1% by weight, and usually in the range 0.001-0.5% e.g. between 0.01-0.25%, between 0.01-0.1%. For instance, the total amount of multifunctional organic peroxide(s) added may be about 0.75%, 0.5%, 0.25%, 0.2%, 0.1%, 0.075%, 0.05%, 0.025%, 0.01%, or 0.005% (by weight) of the total liquid sample. A typical amount is about 0.05%.

Inactivators can be used over a wide pH range e.g. between pH 5 and 10, between pH 6 and 9, or at pH 7±0.5. Inactivation may occur in the presence of a buffer (which may be present in a composition together with the inactivator), but this is usually not necessary.

Inactivators will be used with a combined temperature/time scheme for a desired result in any particular situation, and these two factors can be varied while achieving substantially the same result.

Inactivation will be faster at elevated temperatures, and so the inactivation time period may be shortened. Depending on the situation, an inactivation temperature can, for example, be kept as low as 0° C. with a long inactivation time (e.g. several hours or a few days), or as high as 60° C. for a short time (e.g. for only a few minutes). At higher temperatures, however, many functional proteins or antigens will be harmed or destroyed, and so a preferred treatment will usually utilise a lower temperature (e.g. <30° C.) for a longer time. The effect of these parameters in any particular situation can easily be tested.

Inactivators will be used at a temperature which enables the compounds to inactivate a desired microorganism in the sample of interest over the desired treatment period. Thus inactivation may take place at any suitable temperature e.g. between 0-60° C., between 10-50° C., between 15-40° C., between 15° C.-25° C., between 19-23° C., etc. Inactivation will typically occur at a substantially constant temperature e.g. ±2° C., ±1° C. In some embodiments, however, inactivation uses phases at different temperatures e.g. a first phase at a low temperature (e.g. at between 2-8° C., such as about 4° C.) and a second phase at a higher temperature, typically at least 10° C. higher than the first phase (e.g. at between 25-50° C., such as about 37° C.), or a first phase at a higher temperature e.g. at between 25-50° C., such as about 37° C.), followed by a second phase at a lower temperature e.g. at between 2-8° C., such as about 4° C.).

A two-phase process is particularly useful where the multifunctional peroxide is being used for both inactivation and nucleic acid degradation. In a typical scheme, the lower temperature phase can favour virus inactivation whereas the higher temperature phase can favour nucleic acid degradation.

Inactivators will be used for sufficient time to inactivate microorganisms in the sample of interest at a desired temperature, ideally without reducing a desired microorganism's immunogenicity. Inactivation treatment typically lasts for between 15 minutes and 72 hours e.g. 6-48 hours, 12-36 hours, 18-26 hours, or about 16 or about 24 hours.

Depending on the nature of the microorganism to be inactivated and the industrial setting, a skilled person can select a suitable combination of (i) inactivation time, (ii) concentration of inactivation agent, and (iii) inactivation temperature. In practice, inactivation treatment for vaccine antigens typically lasts for up to 72 hours, but for practical reasons processing times up to 24 hours or shorter are preferred. However, much longer inactivation time up to several weeks have also been used, for example to detoxify bacterial antigen. For robust antigens, or for the inactivation of microorganisms in waste materials, higher inactivating agent concentrations and short inactivation times of only minutes or a few hours may be chosen.

The process of inactivation or of degrading nucleic acids may be performed one or more times (i.e. a multifunctional organic peroxide is added to the sample, is allowed to act on the sample, and then further multifunctional organic peroxide is added, etc.), using repetition to achieve or ensure higher levels of degradation than achieved by a single round of treatment. For example, the process may performed twice. The conditions including time, temperature and concentration of each round may be the same or different. Conditions may be varied so that different rounds may have a different focus e.g. one round to favour inactivation, another round to favour nucleic acid degradation, etc. Any two rounds preferably use the same multifunctional organic peroxide, but as an alternative they can use different multifunctional organic peroxides. Between two rounds in which multifunctional organic peroxides are used, a process can involve a step in which residual multifunctional organic peroxide is removed and/or degraded, but in some embodiments a second round can proceed without this removal.

Combination Treatments

Inactivators of the present invention may be used in combination with alkylating agents, i.e. substances that introduce an alkyl radical into a compound. Suitable alkylating agents include monoalkylating agents, such as β-propiolactone (BPL). BPL is a monoalkylating agent used for inactivation of viruses in the preparation of many vaccines [2]. BPL reacts with various biological molecules including nucleic acids where it causes structural modification by alkylation and depurination.

Thus, where a process of the invention involves a step in which a multifunctional organic peroxide is used, the process can also involve a step in which an alkylating agent is used. Rather than using a multifunctional organic peroxide and an alkylating agent simultaneously, these two steps are preferably performed separately i.e. a multifunctional organic peroxide is used and then an alkylating agent is used later, or a multifunctional organic peroxide is used after an alkylating agent has already been used.

Thus, for instance, the invention provides a process for treating a microorganism-containing sample, comprising contacting the sample with, in either order, (i) a multifunctional organic peroxide and (ii) an alkylating agent such as BPL.

Similarly, the invention provides a method for preparing a pharmaceutical composition, comprising steps of: (i) contacting a microorganism-containing sample with, in either order, a multifunctional organic peroxide and an alkylating agent; (ii) preparing the pharmaceutical composition from the product of step (i). Step (i) with both treatments achieves very good inactivation of microorganisms.

The invention also provides a liquid composition comprising two or more of (i) reaction products of a microorganism and a multifunctional organic peroxide (ii) reaction products of a microorganism and an alkylating agent, and/or (iii) reaction products of a microorganism, a multifunctional organic peroxide and an alkylating agent. The composition may include β-hydroxypropionic acid.

The invention provides a process for treating a sample, comprising contacting the sample with a multifunctional organic peroxide, wherein the sample is the reaction product of a microorganism-containing sample and an alkylating agent such as BPL. Conversely, the invention also provides a process for treating a sample, comprising contacting the sample with an alkylating agent such as BPL, wherein the sample is the reaction product of a microorganism-containing sample and a multifunctional organic peroxide. The invention also provides a method for preparing a pharmaceutical composition, comprising a step of using the treated sample resulting from either of these two processes.

As mentioned above, when used in combination with an alkylating agent, at least one round of treatment is by an alkylating agent and at least one round of treatment is by a multifunctional organic peroxide. The sample may be treated with an alkylating agent in a first round of inactivation and with a multifunctional organic peroxide in a second round of inactivation, or alternatively with a multifunctional organic peroxide in a first round of inactivation and with an alkylating agent in a second round of inactivation. Further rounds of inactivation may be with either an alkylating agent or a multifunctional organic peroxide (or with any other inactivator).

The conditions including time, temperature and concentration of each round of treatment may be the same or different. Useful conditions for treatment by BPL are described below:

BPL is typically added to a final concentration of less than 1% by volume (e.g. less than 1%, 0.75%, 0.5%, 0.25%, 0.2%, 0.1%, 0.075%, 0.05%, 0.025%, 0.01%, or 0.005%). Preferably, BPL is used at between 0.1% and 0.01%.

Alkylating agent is preferably added to a buffered aqueous sample and the pH of the solution is preferably maintained between 5 and 10. More preferably the pH of the solution is maintained between 6 and 9. Even more preferably the pH of the solution is maintained between 7 and 8.

Between the consecutive treatments by an alkylating agent, there may be an alkylating agent removal step, but the alkylating agent may be added for the second treatment without removing any alkylating agent remaining from the first treatment. Similarly, if a multifunctional organic peroxide has been used then it may be removed prior to treatment by alkylating agent.

Treatment with the alkylating agent, particularly with BPL, may involve phases with different temperatures. For instance, there may be a first phase at a low temperature (e.g. at between 2-8° C., such as about 4° C.) and a second phase at a higher temperature, typically at least 10° C. higher than the first phase (e.g. at between 25-50° C., such as about 37° C.). This two-phase process is particularly useful where the alkylating agent is being used for both inactivation and DNA degradation. In a typical scheme, virus inactivation occurs during the lower temperature phase, and DNA degradation occurs during the higher temperature phase. As described in more detail below, an increased temperature can also facilitate removal of a heat-sensitive alkylating reagent.

The alkylating agent and any residual side products are preferably removed prior to final formulation of a pharmaceutical. Thus a final composition can contain less than 0.1% free propionic acid and BPL combined (e.g. less than 0.1%, 0.05%, 0.025%, 0.01%, 0.005%, 0.001%, or 0.01%. Preferably, a final pharmaceutical composition contains less than 0.01% BPL.

BPL can conveniently be removed by heating, to cause hydrolysis into the non-toxic β-hydroxypropionic acid. The length of time required for hydrolysis depends on the total amount of BPL and the temperature. Higher temperatures given more rapid hydrolysis, but the temperature should not be raised so high as to damage the active proteinaceous ingredients. Heating to about 37° C. for 2-2.5 hours is suitable for removing BPL. DNA fragmentation occurs mainly during the BPL hydrolysis step at 37° C. rather than during the virus inactivation step at 2-8° C.

Pharmaceutical Compositions and Products

The invention provides a method for preparing a pharmaceutical composition, comprising a first step of contacting a microorganism-containing sample (usually a liquid sample) with a multifunctional organic peroxide to inactivate microorganisms therein, followed by a step of preparing a pharmaceutical composition from the inactivated material. The inactivated material may be used directly for preparing the pharmaceutical, or it may be subject to further processing e.g. dilution, purification, combination with other active ingredients, combination with inactive pharmaceutical ingredients, etc.

For example, the invention provides a method for preparing a vaccine, comprising a first step of contacting a virus-containing sample (e.g. a liquid sample, such as a culture fluid) with a multifunctional organic peroxide to inactivate the virus, followed by a step of preparing a pharmaceutical composition from the inactivated virus. The inactivated virus may be used directly for preparing the vaccine, or it may be subject to further processing e.g. dilution, further purification of virus components, combination with other vaccine antigens (viral and/or bacterial), combination with buffer(s), combination with adjuvants, etc.

This process may include an initial step of preparing the microorganism-containing sample e.g. a step of viral or bacterial culture.

After growing viruses, an inactivating agent may be used on purified virions e.g. on virions present in a clarified cell culture, or on virions purified from such a clarified cell culture. A method may involve removing cellular material by clarification, and then purification of virions from the clarified cell culture e.g. by chromatography. The inactivating agent maybe used on virions purified in this manner, or after a further optional step of ultrafiltration/diafiltration. As mentioned above, the multifunctional organic peroxide can, in addition to inactivating the virus, degrade any residual DNA from the cell substrate on which the virus was grown.

The inactivating agent may be used before or after a step of endotoxin removal has taken place.

A vaccine composition may be prepared by purification of immunogenic protein(s) from inactivated virus e.g. as in the preparation of split or surface antigen vaccines from inactivated influenza viruses.

Viruses for inactivation may be propagated on any suitable substrate e.g. in a cell line culture, in a primary cell culture, in eggs, etc. Cell culture will often use mammalian cells, such as hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [11-13]. Suitable dog cells are e.g. kidney cells, as in the CLDK and MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [14-17], derived from Madin Darby canine kidney; Vero cells [18-20], derived from African green monkey (Cercopithecus aethiops) kidney; or PER.C6 cells [21], derived from human embryonic retinoblasts. These cell lines are widely available e.g. from the American Type Cell Culture (ATCC) collection [22], from the Coriell Cell Repositories [23], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As well as using mammalian cells, viruses can be grown on avian cells or cell lines (e.g. see refs. 24-26), including cell lines derived from ducks (e.g. duck retina) or hens e.g. chicken embryo fibroblasts (CEF), etc. Examples include avian embryonic stem cells [24,27], including the EBx cell line derived from chicken embryonic stem cells, EB45, EB14, and EB14-074 [28].

One useful cell line is MDCK [29-31], derived from Madin Darby canine kidney. The original MDCK cell line is available from the ATCC as CCL-34. Derivatives of MDCK cells may also be used. For instance, reference 14 discloses a MDCK cell line that was adapted for growth in suspension culture ('MDCK 33016', deposited as DSM ACC 2219). Similarly, reference 32 discloses a MDCK-derived cell line that grows in suspension in serum-free culture CB-702', deposited as FERM BP-7449). Reference 33 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 34 discloses MDCK cell lines with high susceptibility to infection, including 'MDCK.5F1' cells (ATCC CRL-12042). Any of these MDCK cell lines can be used.

Virus may be grown in suspension culture (e.g. see refs. 14, 35 & 36) or in adherent culture. One suitable MDCK cell line for suspension culture is MDCK 33016 (deposited as DSM ACC 2219). As an alternative, microcarrier culture can be used.

Viruses may be grown in serum-free culture media and/or protein free media. A medium is referred to as a serum-free medium in the context of the present invention if it contains no additives from serum of human or animal origin. Protein-free is understood to mean cultures in which multiplication of the cells occurs with exclusion of proteins, growth factors, other protein additives and non-serum proteins, but can optionally include exogenous proteins such as trypsin or other proteases that may be necessary for viral growth.

The invention can also be used to prepare materials which are not themselves pharmaceutical compositions, but which are used during preparation of pharmaceutical compositions. For example, the invention provides a method for manufacturing a safe pharmaceutical product, such as a recombinant protein molecule from a fermentation culture process, by using a multifunctional organic peroxide to inactivate existing or potential contaminating viruses. Viruses that might be present or introduced into such processes are, for example retroviruses which are present in many permanent cell lines, particularly in rodent cells, such as CHO (chinese hamster ovary) cells or mouse myeloma cells. Other contaminants may be animal viruses originating from animal-derived raw material, such as porcine trypsin, medium supplements of bovine origin, or protein hydrolysates of animal origin. The inactivation agent can be introduced into the manufacturing process at almost any step: it may be used for a pre-treatment of raw materials, buffers, media and other starting materials, it may be applied during or after harvesting the raw bulk material (such as a fermenter harvest), or during or after the subsequent concentration and purification steps. However, for practical reasons one may prefer to perform the inactivation early during the process to avoid carrying active microorganisms through the process.

Pharmaceutical compositions usually include components in addition to their antigens e.g. they typically include one or more pharmaceutical carrier(s) and/or excipient(s). A thorough discussion of such components is available in reference 37. A vaccine composition may also include an adjuvant e.g. as disclosed in references 38 and 39 (for example, an adjuvant comprising one or more aluminium salts, or comprising a submicron oil-in-water emulsion).

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions can include a physiological salt, such as a sodium salt e.g. to control tonicity. Sodium chloride (NaCl) is typical, which may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg, e.g. between 240-360 mOsm/kg, or between 290-310 mOsm/kg.

Pharmaceutical compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

Pharmaceutical compositions typically have a pH between 5.0 and 9.5 e.g. between 6.0 and 8.0.

Pharmaceutical compositions are preferably sterile.

Pharmaceutical compositions preferably non-pyrogenic e.g. containing <1 EU (endotoxin unit, a standard measure) per dose, and preferably <0.1 EU per dose.

Pharmaceutical compositions are preferably gluten free.

Pharmaceutical compositions may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate. The detergent may be present only at trace amounts.

A composition may include material for a single administration, or may include material for multiple immunizations (i.e. a 'multidose' kit). The inclusion of a preservative is useful in multidose arrangements. As an alternative (or in addition) to including a preservative in multidose compositions, the compositions may be contained in a container having an aseptic adaptor for removal of material.

Pharmaceutical compositions, and in particular vaccines, are typically administered in a dosage volume of about 0.5 ml, although a half dose (i.e. about 0.25 ml) may be administered to children.

Pharmaceutical compositions can be administered in various ways. The most preferred route is by intramuscular injection (e.g. into the arm or leg), but other available routes include subcutaneous injection, intranasal, oral, intradermal, transcutaneous, transdermal, etc.

Pharmaceutical compositions are suitable for administration to animal (and, in particular, human) patients, and thus include both human and veterinary uses. They may be used in a method of raising an immune response in a patient, comprising the step of administering the composition to the patient.

The immune response raised by these methods will generally include an antibody response, preferably a protective antibody response. Methods for assessing antibody responses, neutralizing capability and protection after viral vaccination are well known in the art. For influenza virus, for instance, human studies have shown that antibody titers against HA are correlated with protection.

As mentioned above, a vaccine composition can include one or more adjuvant(s), which can function to enhance the immune responses (humoral and/or cellular) elicited in a patient who receives the composition. A useful adjuvant can comprise one or more aluminium salts. Another useful adjuvant can comprise an oil-in-water emulsion. Other useful adjuvants are known in the art.

The adjuvants known as aluminum hydroxide and aluminum phosphate may be used, singly or in combination. These names are conventional, but are used for convenience only, as neither is a precise description of the actual chemical compound which is present (e.g. see chapter 9 of reference 40). The invention can use any of the "hydroxide" or "phosphate" adjuvants that are in general use as adjuvants. The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Various useful oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 1 μm in diameter, with these small sizes being achieved with a microfluidiser to provide stable emulsions. Droplets with an average diameter which is <220 nm are preferred as they can be subjected to filter sterilisation. Useful adjuvants can include squalene and/or polysorbate 80. Suitable adjuvants which can be used include those known as MF59 and AS03.

Immunogenic pharmaceutical compositions can be administered by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Host Cell DNA

As mentioned above, multifunctional organic peroxides can be used according to the invention to degrade nucleic acid. This is particularly useful for degrading DNA, such as host cell DNA e.g. which remains present after growth of a virus in a cell culture.

For degrading nucleic acids, treatment with a multifunctional organic peroxide ideally continues until the nucleic acid includes more than 10 abasic nucleotide residues per $10^8$ base pairs e.g. until it includes more than 10 abasic nucleotide residues per $10^7$ base pairs, more than 10 abasic nucleotide residues per $10^6$ base pairs, or more than 10 abasic nucleotide residues per $10^5$ base pairs. The presence of abasic residues (and in particular following depurination) can lead to cleavage of the nucleic acid backbone and thus to fragmentation.

For degrading nucleic acids, treatment with a multifunctional organic peroxide ideally continues until the average length of remaining DNA strands is less than 1000 base pairs (e.g. less than 900, 800, 700, 600, 500, 400, 300, 200, 150, 100, 75, or 50 base pairs). Preferably, the length of remaining DNA is less than 500 base pairs and, more preferably, is less than 200 base pairs. The size of any remaining DNA may be measured by standard techniques, including capillary gel electrophoresis or nucleic acid amplification technology. These remaining short fragments are small enough that they are unlikely or unable to code for a functional protein, to be transposed into a human recipient's chromosome, or otherwise be recognized by recipient DNA replication machinery. Generally, nucleotide sequences capable of being translated to a functional protein require promoter regions, start codons, stop codons, and internal coding sequences for functional proteins. Where DNA damage occurs, as by treatment with a multifunctional organic peroxide, many of these regions are altered or destroyed, such that transcription and/or translation can longer occur.

A pharmaceutical composition preferably contains less than 10 ng (preferably less than 1 ng, and more preferably less than 100 pg) of residual DNA per dose, although trace amounts of host cell DNA may still be present. In general, the host cell DNA that it is most desirable to exclude from compositions of the invention is DNA that is longer than 200 base pairs.

Measurement of residual host cell DNA is now a routine regulatory requirement for biologicals and is within the normal capabilities of the skilled person. The assay used to measure DNA will typically be a validated assay [41,42]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [43]; immunoassay methods, such as the Threshold™ System [44]; and quantitative PCR [45]. These methods are all familiar to the skilled person, although the precise characteristics of each method may depend on the host cell in question e.g. the choice of probes for hybridization, the choice of primers and/or probes for amplification, etc. The Threshold™ system from *Molecular Devices* is a quantitative assay for picogram levels of total DNA, and has been used for monitoring levels of contaminating DNA in biopharmaceuticals [44]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 46.

In relation to canine cells in particular, such as MDCK cells, analysis of the genome reveals 13 coding sequences <500 bp in length, 3 sequences <200 bp and 1 sequence <100 bp. Thus fragmentation of DNA to <200 bp removes substantially all coding sequences, and it is highly unlikely that any fragment would actually correspond to one of the 3 genes around that length (namely: secretin at 81 bp; PYY at 108 bp; and osteocalcin at 135 bp).

Short degraded DNA can be removed from a composition more readily than long DNA and so the invention is useful for reducing the amount of residual DNA in a pharmaceutical composition. After treating a microorganism-containing composition to degrade free DNA, the DNA degradation products can optionally be removed. For a virus-containing sample, therefore, the DNA degradation products can be separated from virus. Small soluble degraded DNA fragments can readily be separated from viruses e.g. by anion exchange chromatography, by size-based methods, etc.

Influenza Vaccines

The invention is useful for inactivating influenza viruses during vaccine manufacture. Vaccines for influenza virus may be based on whole virions, 'split' virions, or on purified surface antigens (including hemagglutinin and, usually, also including neuraminidase). The invention can be used during manufacture of any of these types of vaccine.

Influenza virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 47-52, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarkosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [53,54]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Influenza virus strains for use in vaccines change from season to season. In inter-pandemic periods, vaccines typically include two influenza A strains (H1N1 and H3N2) and one influenza B strain, and trivalent vaccines are typical. The invention may also use pandemic viral strains (i.e. strains to which the vaccine recipient and the general human population are immunologically naïve, in particular of influenza A virus), such as H2, H5, H7 or H9 subtype strains, and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [55], including antigens from two influenza A virus strains and two influenza B virus strains, or three influenza A virus strains and one influenza B virus strain.

Once an influenza virus has been purified for a particular strain, it may be combined with viruses from other strains e.g. to make a trivalent vaccine as described above. It is preferred to treat each strain separately and to mix monovalent bulks to give a final multivalent mixture, rather than to mix viruses and degrade DNA from a multivalent mixture.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used (e.g. for reassortment or reverse genetics), it is preferably one that has been approved for use in human vaccine production e.g. as in Ph Eur general chapter 5.2.3.

MODES FOR CARRYING OUT THE INVENTION

Known Inactivators

Figure 1:
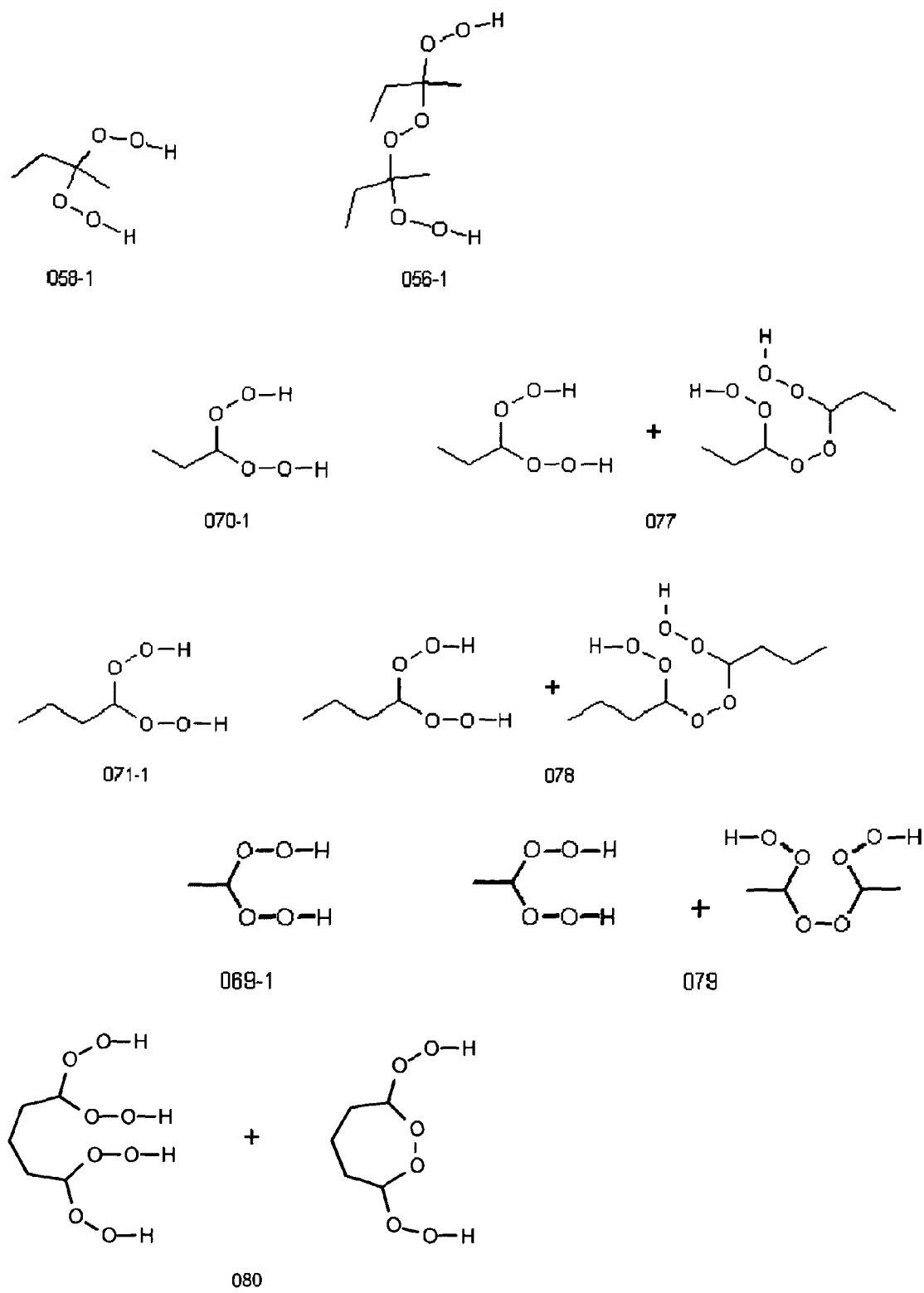
FIG. 1 shows the structures of various inactivators of the invention.

Known inactivators (β-propiolactone, ethyleneimine, N-acetyl ethyleneimine, formalin) were tested against four viruses: (i) a type 3 reovirus, non-enveloped, with a dsRNA genome; (ii) a HSV-1 herpesvirus, enveloped with a dsDNA genome; (iii) an adenovirus 5, non-enveloped with a dsDNA genome; and (iv) an avian C-type retrovirus, enveloped with a ssRNA genome. The reovirus is a small non-enveloped virus with a double capsid layer, and such viruses are highly resistant to inactivation (surpassed only by tubercle bacilli and bacterial spores [56]).

Results are expressed in Table 1 as a log 10 reduction factor in viral titre after treatment:

| Virus | Inactivation | Reduction |
|---|---|---|
| (i) | BPL, 0.05%, 16 hours, 2-8° C. (then 3 hours at 37° C. to remove BPL) | 2.3-3.8 |
| | Ethyleneimine, 0.05%, 16 hours, 2-8° C. (then 3 hours at 37° C.) | 0.65 |
| | NAc-ethyleneimine, 0.05%, 16 hours, 2-8° C. (then 3 hours at 37° C.) | 1.15 |
| | 37% formaldehyde 0.05%, 16 hours, 2-8° C. | ~0 |
| | 37% formaldehyde 0.05%, 3 days, 2-8° C. | 0.9 |
| | 37% formaldehyde 0.05%, 6 days, 2-8° C. | 1.55 |
| | 37% formaldehyde 0.05%, 17 hours, 19-23° C. | 1.7 |
| | 37% formaldehyde 0.05%, 24 hours, 19-23° C. | 2.1 |
| (ii) | BPL, 0.05%, 16 hours, 2-8° C. (then 3 hours at 37° C. to remove BPL) | 4.5 |
| | 37% formaldehyde 0.05%, 3 days, 2-8° C. | 2.8 |
| | 37% formaldehyde 0.05%, 6 days, 2-8° C. | 2.95 |
| | 37% formaldehyde 0.05%, 17 hours, 19-23° C. | 2.95 |
| | 37% formaldehyde 0.05%, 24 hours, 19-23° C. | 3.25 |
| (iii) | BPL, 0.05%, 16 hours, 2-8° C. (then 3 hours at 37° C. to remove BPL) | 2.7 |
| | 37% formaldehyde 0.05%, 3 days, 2-8° C. | ≥3.4, ≤6.65 |
| | 37% formaldehyde 0.05%, 6 days, 2-8° C. | ≥3.4, ≤6.65 |
| | 37% formaldehyde 0.05%, 17 hours, 19-23° C. | ≥6.65 |
| | 37% formaldehyde 0.05%, 24 hours, 19-23° C. | ≥6.65 |
| (iv) | BPL, 0.05%, 16 hours, 2-8° C. (then 3 hours at 37° C. to remove BPL) | ≥5.15, ≤7.15 |
| | 37% formaldehyde 0.05%, 16-24 hours, 15° C. | 0.6-1.0 |
| | 37% formaldehyde 0.05%, 16-24 hours, 20° C. | 1.3-1.8 |
| | 37% formaldehyde 0.05%, 16-24 hours, 24° C. | 1.5-2.2 |

These data show that the two main inactivators used in human vaccines (BPL and formaldehyde) cannot meet all needs. Even low levels of infectivity of stable viruses mean that material may not be safe for downstream use (e.g. as a diagnostic reagent, or as a vaccine or other medicinal product).

New Inactivators

Due to its stability a reovirus model was established to assess the activity of new inactivators. Mammalian orthoreovirus, type 3 (strain Dearing, ATCC VR-824), was grown in L929 mouse connective tissue cells (ATCC Cl-1). Virus stocks were made from cell-free culture supernatants of infected cultures and were aliquoted then stored below −60° C. For inactivation studies the virus was thawed, then 0.05% inactivator was added (1:2000 by volume), and the mixture was incubated in cold (2-8° C.), room temperature (measured as 19-23° C.) or at 37° C. for fixed periods. To permit comparison with BPL (i) the inactivation reactions were briefly raised to 37° C. and (ii) sodium thiosulfate was added at the end of inactivation (20 μl of a 1.4M stock solution per ml inactivation solution). Samples were then tested for residual infective virus by standard titration. Tenfold serial dilutions of the virus preparation were inoculated into L929 cultures in microtitre plates. Growing virus produces a cytopathic effect after 5-6 days, visible by microscope. Titres were calculated by the Spearman-Kaerber method [57] and are expressed as log 10 $TCID_{50}$ per ml. Where residual titres were below the limit of detection (1.5 log 10 $TCID_{50}$ per ml) they are expressed as the difference between the control sample titre and ≤1.5. Such reduction are shown by a "≥" symbol.

Influenza virus was used in a second test. It is less stable than reovirus. Virus titrations were performed essentially as described for reovirus, but with MDCK cells not L929. In addition, stability of its envelope hemagglutinin glycoprotein (an important vaccine immunogen) was assessed. It can be functionally assayed by the hemagglutination test. For a quantitative HA assay the virus preparation was serially diluted (log 2 dilutions) in PBS and incubated with 0.5% chicken red blood cells in PBS. After incubation at ambient temperature the HA reaction was evaluated. Activity is expressed as the reciprocal of the highest virus dilution which still causes a clear hemagglutination, and results are shown as the titre before and after inactivation.

Various inactivators were tested, with the numbering from FIG. 1 and/or Table 18. All were at a concentration of 0.05%, and this is the total inactivator concentration when mixtures were used.

Results with reovirus were as follows (Table 2):

| Inactivator | Conditions | Reduction |
|---|---|---|
| BPL | 16 hours, 2-8° C.; then 3 hours at 37° C. | 2.5 |
| 054 | 16 hours, 2-8° C.; then 3 hours at 37° C. | ≥3.8 * |
| 069-1 | 16 hours, 2-8° C.; then 3 hours at 37° C. | ≥6.9 |
| 069-1 | 24 hours, 19-23° C. | ≥7.0 |
| 079 | 16 hours, 2-8° C.; then 3 hours at 37° C. | 3.5 |
| 079 | 24 hours, 19-23° C. | 4.5 |
| 070-1 | 16 hours, 2-8° C.; then 3 hours at 37° C. | 5.0 |
| 070-1 | 24 hours, 19-23° C. | 5.8 |
| 070-1 | 48 hours, 19-23° C. | 5.5 |
| 070-1 | 16 hours, 37° C. | 7.65 |
| 070-1 | 24 hours, 37° C. | ≥7.9 |
| 077 | 24 hours, 19-23° C. | ≥7.7 |
| 071-1 | 16 hours, 2-8° C.; then 3 hours at 37° C. | 4.0 |
| 078 | 24 hours, 19-23° C. | 3.3-5.4 |
| 078 | 16 hours, 37° C. | ≥7.75 |
| 058-1 | 16 hours, 2-8° C.; then 3 hours at 37° C. | 3.5 |

-continued

| Inactivator | Conditions | Reduction |
|---|---|---|
| 056-1 | 16 hours, 2-8° C.; then 3 hours at 37° C. | 3.3 |
| 080 | 16 hours, 2-8° C.; then 3 hours at 37° C. | ≥6.9 |
| For comparison (single peroxide compounds) | | |
| $H_2O_2$ | 16 hours, 2-8° C.; then 3 hours at 37° C. | 0.45 |
| 072 | 16 hours, 2-8° C.; then 3 hours at 37° C. | 0.9 |

* Residual cytotoxicity interfered with virus titration and did not permit evaluation of the full inactivation capacity The BPL figure confirms that reovirus inactivation is difficult, as seen in the previous results. All of the inactivators with multiple peroxides gave better inactivation than BPL (and than formaldehyde in the previous experiments). The compound with a single peroxide (072) performed poorly. Compounds with shorter chain lengths (lower than C4) gave the best results. Higher temperatures gave better results, although long incubation at 37° C. is not ideal for antigens which may not have good thermal stability. Shorter times at higher temperatures may be optimal.

Results with influenza virus were as follows (Table 3):

| Inactivator | Conditions | Reduction | HA before/after |
|---|---|---|---|
| BPL | 16 hours, 2-8° C.; then 3 hours at 37° C. | ≥7.15 | 1024/1024 |
| 069-1 | 16 hours, 2-8° C.; then 3 hours at 37° C. | ≥7.1 | 1024/1024 |
| 079 | 16 hours, 2-8° C.; then 3 hours at 37° C. | ≥7.1 | 1024/1024 |
| 079 | 24 hours, 19-23° C. | ≥6.9 | 1024/1024 |
| 070-1 | 16 hours, 2-8° C.; then 3 hours at 37° C. | ≥7.0 | 1024/1024 |
| 077 | 24 hours, 19-23° C. | ≥7.1 | 1024/1024 |
| 071-1 | 16 hours, 2-8° C.; then 3 hours at 37° C. | 5.0 | 1024/1024 |
| 078 | 24 hours, 19-23° C. | 5.75 | 1024/1024 |
| 058-1 | 16 hours, 2-8° C.; then 3 hours at 37° C. | ≥7.15 | 1024/1024 |
| 056-1 | 16 hours, 2-8° C.; then 3 hours at 37° C. | ≥7.15 | 1024/1024 |
| 080 | 16 hours, 2-8° C.; then 3 hours at 37° C. | 7.0 | 1024/1024 |

Thus inactivation of influenza virus to below the detection limit was routinely achieved. Again, compounds with shorter chain lengths gave the best results, with lower inactivation capacity by molecules with a longer chain length e.g. 071-1, 078 and 080. Moreover, in all cases, and regardless of inactivation temperature, the hemagglutination titre was unaffected by inactivation, indicating that the surface glycoprotein's antigenicity remains intact.

The results with stable, non-enveloped viruses bacteria mean that successful inactivation of bacteria can also be expected. In 1968 Spaulding defined levels of resistance against chemical inactivation and disinfection [56]. According to this ranking, bacteria (except some mycobacteria and spores) are less resistant to chemical inactivation than naked (non-lipid) viruses. Although this ranking has been established decades ago, it remains valid and applicable [58]. Efficacy against a stable, non-enveloped virus thus means that bacteria can also be inactivated by these compounds.

The inactivating capacity of inactivator 069-1 was tested against further viruses. In these studies, concentration, time and temperature were varied to further evaluate suitable conditions for inactivation. Where complete inactivation to below the detection limit of the titration method (≤$10^{1.5}$ $TCID_{50}$/ml) was observed, tests for residual virus with a lower detection limit were partly done. If negative for virus, the results of such "residual virus test" are given by indicating the respective detection limit per mL inactivated sample. Those detection limits depend on the sample volume inoculated into test cultures. For a sample volume of 10 mL, the detection limit was given as $10^{-1.5}$ $TCID_{50}$/ml, for sample volumes of 1 ml the respective detection limit was $10^{-0.5}$ $TCID_{50}$/ml, and for a sample volume of 0.1 ml it was $10^{0.5}$ $TCID_{50}$/ml.

Where residual cytotoxicity in a test culture (indicated by early signs of cell detachment or death in the test cultures) impaired a reliable titer reading, those titration dilutions were not evaluated. In negative titrations the applicable detection limit was accordingly higher, for example ≤$10^{2.5}$ $TCID_{50}$/ml. Cytotoxic reactions were partly observed at the lowest titration dilutions where the inoculum with residues of the inactivating agent and ascorbic acid were left on the test cultures. In residual virus tests with higher sample volumes no cytotoxic effects were seen since larger cultures were used, the inoculum was removed after adsorption of the virus for 1 hour at 37° C., and the cultures were flushed with neutral buffer or medium to remove residual chemicals.

$Log_{10}$ reduction values were then calculated as the difference between the starting titer (measured with a "hold sample" that was exposed to the same conditions but with buffer added without inactivator) and the residual titer after inactivation. Inactivation rates with a "≥" sign indicate complete inactivation to below the detection limit of the applied method. Inactivation rates without that symbol indicate the presence of residual virus.

The following table shows the viruses used and the cell cultures applied for virus titration and for optional residual virus tests using larger sample volumes. It also provides information about the origin of cells and viruses and mentions the incubation periods (days) between cell culture inoculation and the determination of virus titers. The cell cultures were grown in DMEM (Dulbecco modified Eagle's medium) supplemented with 3-5% fetal bovine serum. Test cultures were incubated at 37° C. under an atmosphere containing 5% $CO_2$ and 90% humidity.

| Cell type | Virus | Incubation (days) |
|---|---|---|
| MDCK 33016 (DSM ACC2219) | Influenza viruses. Partly purified virus preparations of different influenza strains: A/Brisbane/59/2007 [H1N1] A/California//7/2009 [H1N1], reassortant X-179A A/Uruguay/716/2007 [H3N2], reassortant NYMC X-175 C B/Brisbane/3/2007 | 4-5 |
| L929 (ATCC CCL-1) | Reovirus 3: Strain Dearing, ATCC VR-824 | 5-7 |
| | MVM (Minute Virus of Mice, a Parvovirus): Strain Crawford, ATCC VR-663 | 9-10 |

| Cell type | Virus | Incubation (days) |
| --- | --- | --- |
| MRC-5 (ATCC CCL-171) | BK-Virus (Polyomavirus); ATCC VR-837 | 10-12 |
| RD-A (European Reference Center for Enteroviruses of the WHO) | ECHO-Virus 6 (Picornavirus): Strain D'Amori, obtained from the Reference-Center for Poliomyelitis and Enteroviruses, Robert-Koch-Institute, Berlin, Germany | 3-5 |
| | Coxsackie A16 (Picornavirus): Strain G-10, obtained from the Reference-Center for Poliomyelitis and Enteroviruses, Robert-Koch-Institute, Berlin, Germany | 3-5 |
| Vero WHO (WHO strain of Vero, distributed by ECACC) | Adenovirus 6: Isolate 524/90: Clinical isolate obtained from Cinical Virology, Robert-Koch-Institute, Berlin, Germany. Identity confirmed by serologically and by PCR. | 8-10 |
| | Rabies virus Flury LEP: Novartis Vaccine strain. (Virus detection via immunostaining with fluorescence-labelled specific antibodies) | 4-5 |
| | HSV-1 (Herpes simplex virus 1): Strain ET, an own isolate. Identity confirmed by independent PCR. | 7-8 |
| | Parainfluenza virus type 3: ATCC VR-93 | 5-6 |

Inactivating agent 069-1 was added at a concentration of 0.025, 0.05, or 0.1% (vol/vol) final concentration and incubated for the indicated time periods. To stop the inactivation at the determined time point, L+ ascorbic acid was added to give a final concentration of 0.2%. This stopping agent was prepared as a 20% stock solution containing 20 g L+ ascorbic acid in 100 mL distilled, sterile water. The solution was then filter sterilized by passing it through a 0.2 µm filter.

Tables 4 to 13 show the inactivation of different model viruses by varying concentrations of agent 069-1 and under different conditions. Most of these viruses are non-enveloped and represent stable viruses which are not easily inactivated by chemical inactivation agents and under conditions applied to preserve the viral antigenicity. Double-stranded viruses (Herpesvirus, Reovirus, Polyomavirus, Adenovirus, and Polyomavirus) were selected because they are more resistant against chemical inactivation and other processing conditions. Most of the viruses have been used as model viruses for validating process inactivation of processes for biopharmaceutical processes [59].

Data for inactivation of different viruses by BPL are provided in table 14. The data in tables 4 to 13 show that 069-1 results in most cases in a superior inactivation.

Analysis of Cellular DNA Damage Induced by Inactivation

The effects of agent 069-1 on cellular DNA were measured by exposing cells culture harvests or influenza-infected cell-free MDCK culture harvests (containing residual cellular DNA) to the inactivating agent and by then analysing the extracted DNA for abasic sites (APS) using a commercial "DNA Damage Quantification Kit" (Biovision). This kit contains an aldehyde reactive probe (ARP) which specifically reacts with aldehyde groups of abasic sites of nucleic acids. After removal of unbound ARP, the DNA is bound to microtiter plate wells and the labelled sites are stained via a peroxidase reaction and a substrate developing a color reaction. The tests kit also contains standards to be used for generating a calibration curve.

DNA extractions were carried out using a QIAsymphony® Virus/Bacteria Mini Kit in the QIAsymphony SP extraction automate using the Complex800_V4 protocol (Qiagen). The DNA concentration of the eluted samples was determined with a NanoPhotometer™ based on adsorption values at 260 nm and 280 nm. For the DNA Damage Quantification Kit, all test samples were then diluted/adjusted in Tris/EDTA (TE) buffer to a final concentration of 0.1 µg/mL DNA. TE buffer served as negative control.

Measuring DNA damage and APS was done according to the instructions of the test kit. Due to strong reactions which exceeded by far the quantitative tests range of the standard curve, attempts were made to compensate this by diluting all labelled and washed samples of one test run by the same rate. Nevertheless extreme colour reactions above a reliable quantitative test range were unavoidable. Thus AP site values above the upper standard curve range of 40 APS per $10^5$ base pairs may be less reliable than those below. Furthermore, high test variability was also observed, which could not be attributed to operator errors or inherent test inconsistencies.

However, DNA from influenza virus infected cell showed particularly high variations when different virus strains were used for infection. This indicates than apoptotically degraded DNA might react differently than normal cell DNA. Thus test was applied in a semi-quantitative, comparative way and by including BPL inactivated samples as a reference and comparator. Consequently quantitative tests results and absolute values (APS per $10^5$ base pairs) should not be compared between different tests but should only be used for comparing different conditions tested within one and the same test run.

The data sets shown below provide results obtained by one comparative test run in separate tables but not mixed results from different test runs in the same table. Except where needed for direct comparison, sample dilutions before adsorption to the test kit microtiter plate were not considered. Thus different APS values may be shown for similar conditions tested in different test runs. APS values above 1 were given as rounded figures without a decimal point.

Comparative results from BPL inactivation were obtained by inactivated samples using a commonly applied 0.05% final concentration of BPL. Inactivation was always applied by adding BPL to the cold virus preparation and by incubation for 16 hours at 2-8° C. The inactivation was then stopped by raising the temperature to 37° C. and by further incubation for 2 hours. At 37° C. the inactivation initially continues at an increased speed, while at the same time BPL is rapidly degraded. Thus the elevated temperature is expected to also impact on DNA damage and/or contributes to secondary reactions on partly damaged DNA.

Inactivation with 069-1 was performed using a standard inactivation time of 16 hours at the concentration and temperature indicated in the tables below. Inactivation was stopped by addition of ascorbic acid. Only for specific studies and for a direct comparison, inactivation with 069-1 were also subject to incubation conditions as used for BPL i.e. 16 hours at 2-8° C. plus 2 hours 37° C.

Table 15 shows the relative APS values (1 being an untreated sample). DNA from cell supernatants infected with 3 different influenza strains (A/Christchurch/16/10 NIB-74, A/Brisbane/10/2010 and A/California/7/09 X-179A) were used. Except for A/California, DNA damage was higher with 069-1 than with BPL and was concentration-dependent.

Table 16 shows relative APS values when influenza infected cell DNA (strain B/Wisconsin/1/2010) was treated with different concentrations of 069-1 as a single inactivation or with two consecutive inactivation rounds. The observed DNA damage was stronger with 069-1 than with BPL, even when lower concentrations of 069-1 were used, and the effects were concentration-dependent. The 2-fold inactivation clearly caused stronger DNA damage than a single inactivation.

Table 17 shows the relative APS values when influenza infected cell DNA (strain B/Wisconsin/1/2010) was treated with BPL first (2-8° C. for 16 hours, then 2 hours 37° C.) and consecutively by inactivation with different concentrations of 069-1. In this series, 069-1 was also used under the same conditions as for a standard BPL inactivation. This inactivation was also stopped by ascorbic acid. With some caution (double-inactivated sample were all high above the measurable range of the test and thus had to be diluted 10-fold before adsorption to the test plate), DNA damage was clearly increased by double treatment with BPL and 069-1. Increasing the inactivation temperature for 069-1 after an initial cold phase to 37° C. for 2 hours also greatly enhanced the DNA damage. Obviously DNA damage caused by BPL can be enhanced not only by a 2-fold BPL treatment but even more so by using a hydroperoxide inactivator, such as 069-1, in addition to BPL.

Synthesis and Stability

The general synthesis of geminal dihydroperoxides can be performed as follows, ideally in the presence of a suitable catalyst:

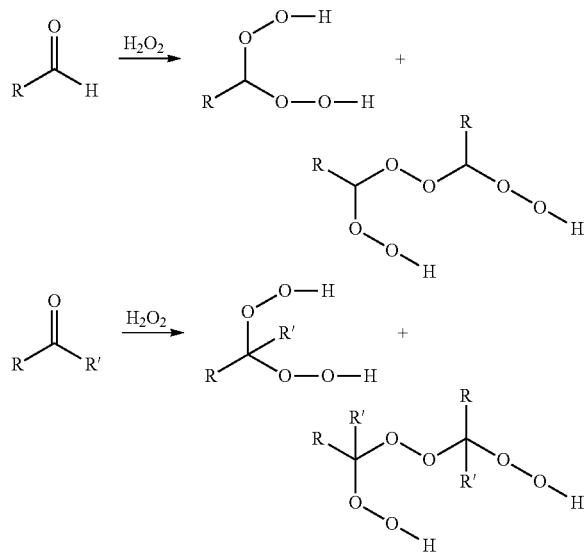

The synthesis is limited by stability and depends on structure. Despite the very high oxygen content (e.g. compound 069-1 has 68% oxygen) some of the compounds are remarkably stable but they can be prone to spontaneous explosion or degradation if handled incorrectly. This effect is increased by shortening the alkyl side chain. Because of safety considerations the compounds may best be supplied as frozen aqueous solutions or frozen solids.

The inactivation capacity of 057 was found to be lost after six months of storage at −20° C. and so it is best used fresh. The same may be true for other compounds and/or mixtures.

Stability of the compounds has been assessed by NMR. Results are as follows:

| Inactivator | Conditions | Degradation |
|---|---|---|
| 057 | PBS: 16 hours, 2-8° C.; then 3 hours at 37° C. | None |
| 057 | PBS: 16 hours, 2-8° C.; then 10 hours at 37° C. | None |
| 057 | PBS: 6 hours, 25° C.; then 3 hours at 37° C. | None |
| 057 | PBS: Addition of sodium thiosulphate | Immediate |
| 070 | PBS: 16 hours, 2-8° C.; then 3 hours at 37° C. | 40% |
| 070 | MEM: 24 hours, 5° C. | <5% |
| 070 | MEM: 24 hours, 25° C. | 15% |
| 070 | MEM: 24 hours, 37° C. | 43% |
| 071 | PBS: 16 hours, 2-8° C.; then 3 hours at 37° C. | None |
| 071 | MEM: 24 hours, 5° C. | 11% |
| 071 | MEM: 24 hours, 25° C. | 15% |
| 071 | MEM: 24 hours, 37° C. | 30% |

PBS = phosphate buffered saline
MEM = Eagle's minimum essential medium

NMR was also used to study the stability of 069-1 in aqueous conditions, and in particular in culture medium. These studies used high resolution 500 MHz NMR with 0.1% 069-1 in DMEM.

Figure 2:
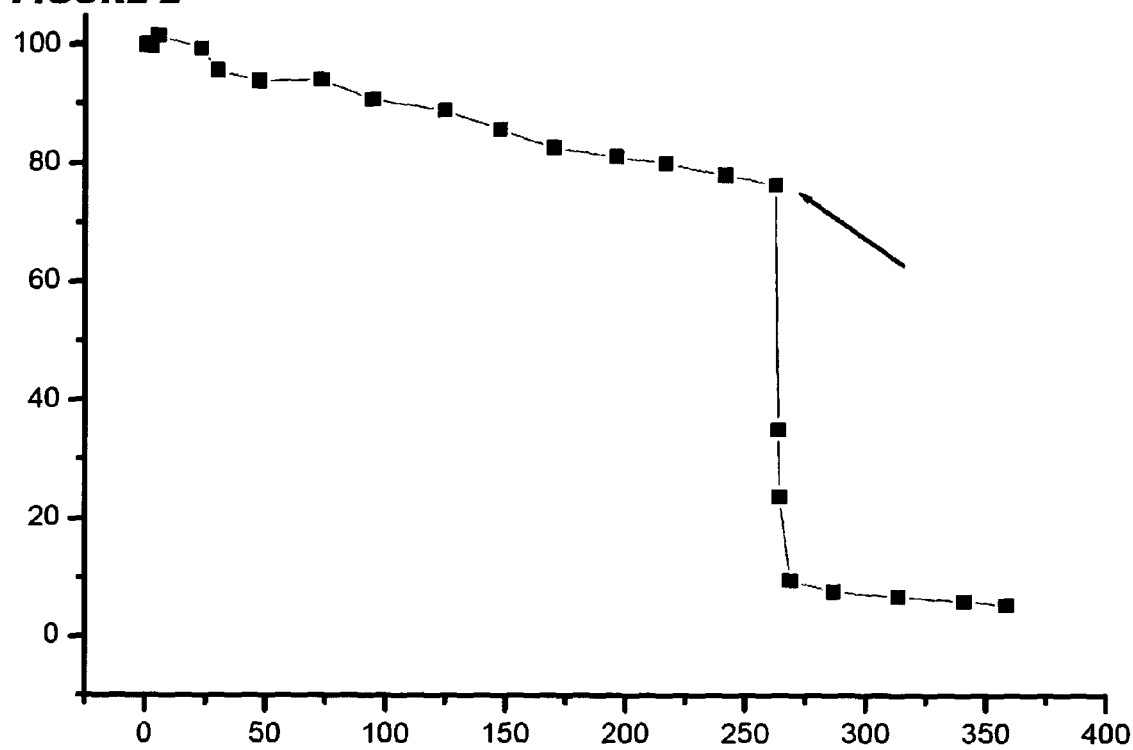
FIGS. 2 to 4 show the content of agent 069-1(%) over time (hours in FIGS. 2 & 3; days in FIG. 4) in DMEM. Arrows indicate the addition of an inactivator (ascorbic acid or glucose).

FIG. 2 shows stability at 25° C., with very slow degradation. After 240 hours (ten days) only 25% had been degraded. Addition of ascorbic acid after 240 hours led to an immediate degradation, which stopped (line levels off) when the ascorbic acid was completely used up and was no longer available to the degradation process. Complete degradation of 069-1 could be observed if more than two moles of ascorbic acid are added to one mole of 069-1.

Figure 3:
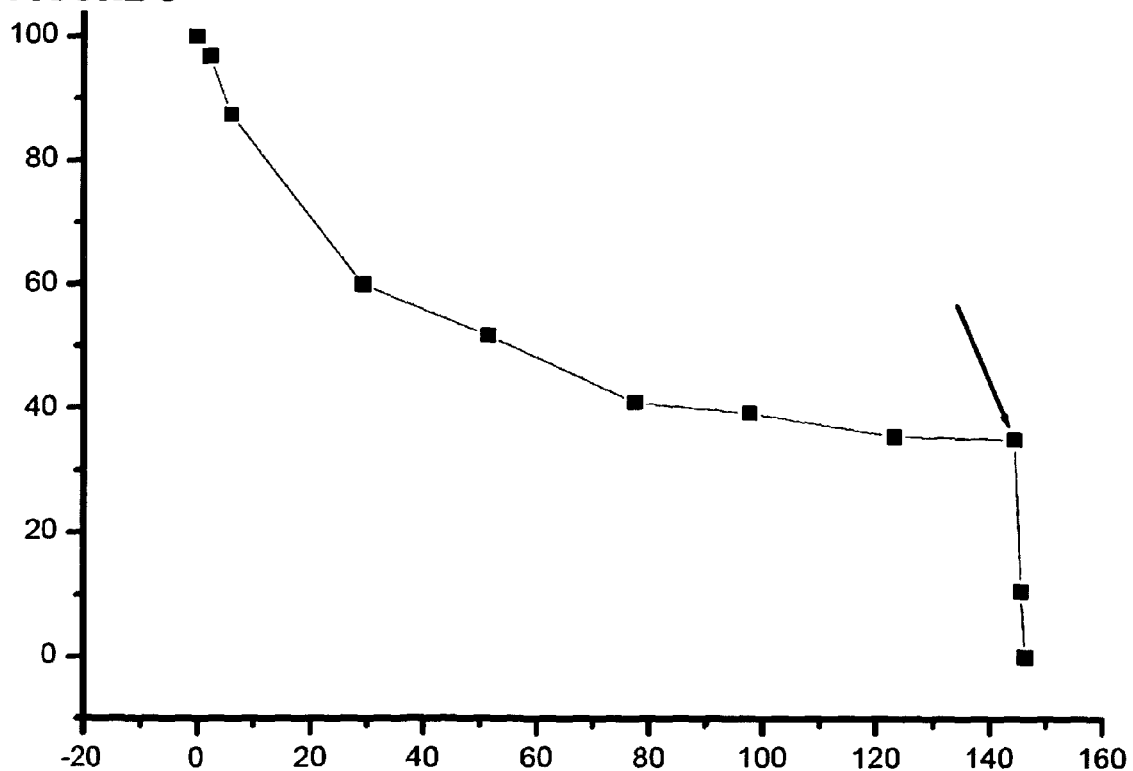

FIG. 3 shows stability at 37° C. Degradation is faster than at 25° C. and after 55 hours 50% has been degraded. Addition of ascorbic acid after 145 hours results in an immediate degradation that can be clearly observed.

Figure 4:
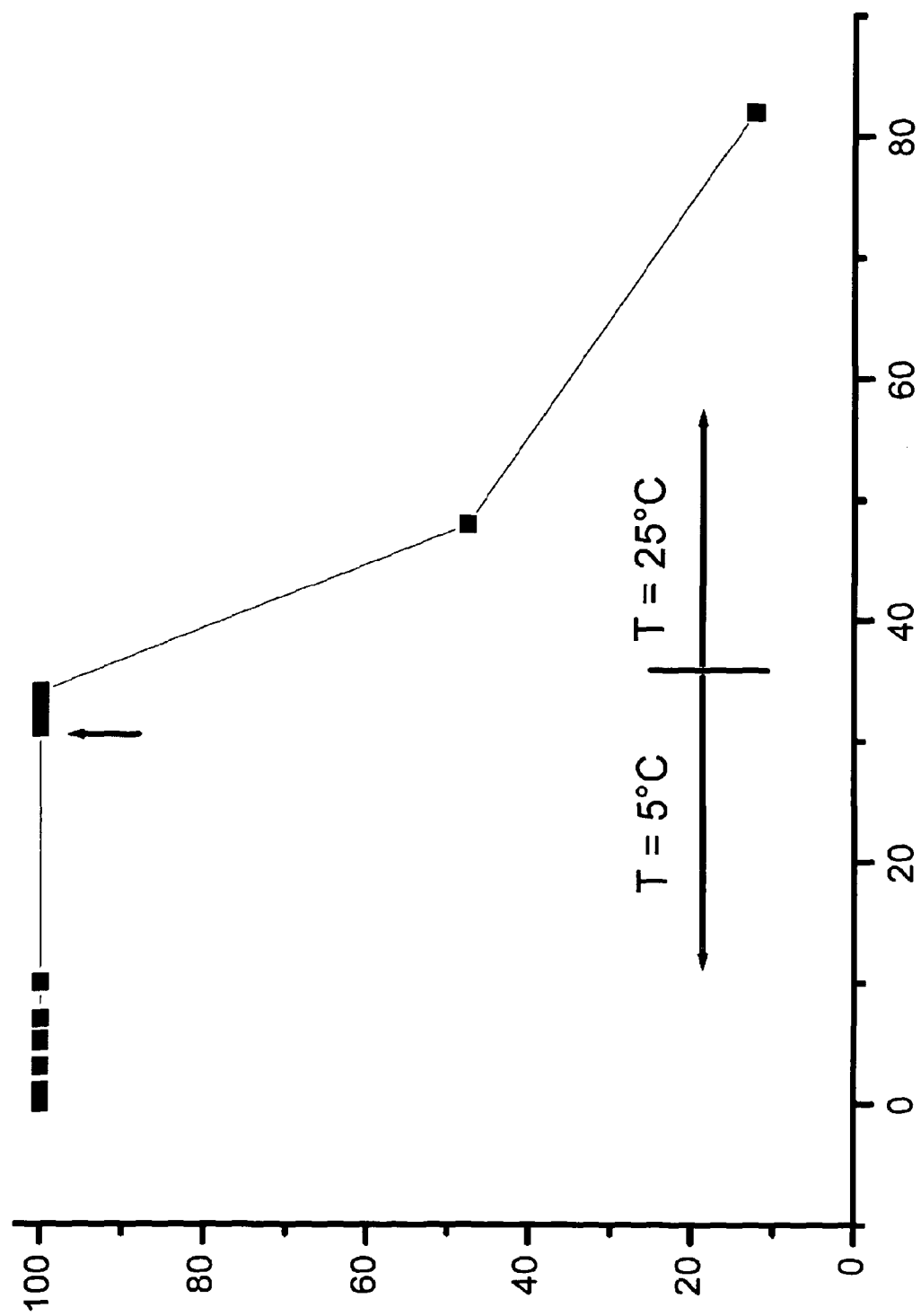

FIG. 4 shows stability at different temperatures and after addition of glucose. There is no degradation at 5° C. in DMEM for more than 30 days. After the addition of glucose (8-fold molar excess) and further storage at 5° C. for five days, still no degradation could be observed. Upon a temperature increase to 25° C. the degradation process starts slowly, but still needs more than 40 days to drop to concentrations of ~10%.

The addition of glucose was tested because many viral growth media contain additional glucose (or similar sugars) and it was important no see if these would degrade the inactivator. At least for lower temperatures, the presence of these sugars does not seem to be a problem.

The high stability of 069-1 in aqueous conditions is surprising because peroxides in general (and in particular short chain peroxides with only 1-5 carbon atoms) are very well known to be susceptible to fast degradation, or even to explosion, as the peroxy group is highly unstable. Agent 069-1 demonstrates an unexpectedly high stability in solution at different temperatures even in complex surroundings like DMEM. As the molecule contains 68% oxygen it possesses a most remarkable and unexpected level of stability for a geminal bishydroperoxide that contains only two carbon atoms. The expected degradation timescale in solution was in the order of a few minutes to a few hours, but FIGS. 2-4 show a high stability for more than 250 hours at 25° C.

It will be understood that the invention has been described by way of example only and modifications may be made whilst remaining within the scope and spirit of the invention.

LRV Tables

TABLE 4

Inactivation of Adenovirus by 069-1

| | | TCID$_{50}$/ml | | TCID$_{50}$/ml after inactivation | | | | |
|---|---|---|---|---|---|---|---|---|
| $t_{IA}$ | $T_{IA}$ | Hold Sample | | Titration | | Res. virus test | LRV | |
| hours | ° C. | log 10 | 95% CI | log 10 | 95% CI | log 10 | log 10 | 95% CI |
| | | | | 0.025% | | | | |
| 16 | RT | 6.60 | ±0.21 | ≤2.50 | ±0.25 | n.d | ≥4.10 | ±0.32 |
| | | | | 0.05% | | | | |
| 6 | RT | 6.45 | ±0.31 | ≤2.50 | ±0.00 | n.d. | ≥3.95 | ±0.31 |
| 16 | RT | 6.30 | ±0.27 | ≤1.50 | ±0.00 | n.d. | ≥4.80 | ±0.27 |
| 16 | RT | 6.35 | ±0.35 | ≤1.50 | ±0.00 | ≤0.5 | ≥5.85 | ±0.35 |
| 16 | 37 | 6.25 | ±0.26 | ≤1.50 | ±0.00 | n.d. | ≥4.75 | ±0.26 |
| | | | | 0.10% | | | | |
| 16 | RT | 6.25 | ±0.31 | ≤1.50 | ±0.00 | n.d. | ≥4.75 | ±0.31 |
| 16 | 37 | 6.30 | ±0.25 | ≤1.50 | ±0.00 | n.d. | ≥4.80 | ±0.25 |

TABLE 5

Inactivation of the BK-Polyomavirus by 069-1

| | | TCID$_{50}$/ml | | TCID$_{50}$/ml after inactivation | | | | |
|---|---|---|---|---|---|---|---|---|
| | $T_{IA}$ | Hold Sample | | Titration | | Res. virus test | LRV | |
| $t_{IA}$ hours | ° C. | log 10 | 95% CI | log 10 | 95% CI | log 10 | log 10 | 95% CI |
| | | | | 0.025% | | | | |
| 16 | RT | 6.05 | ±0.26 | ≤2.40 | ±0.24 | n.d. | ≥3.65 | ±0.36 |
| 16 | 37 | 5.85 | ±0.24 | ≤1.50 | ±0.00 | n.d. | ≥4.35 | ±0.24 |
| | | | | 0.05% | | | | |
| 16 | RT | 5.95 | ±0.24 | ≤1.50 | ±0.00 | n.d. | ≥4.45 | ±0.24 |
| 16 | RT | 6.20 | ±0.28 | ≤1.50 | ±0.00 | ≤−1.5 | ≥7.70 | ±0.28 |
| 16 | 37 | 5.70 | ±0.21 | ≤1.50 | ±0.00 | n.d. | ≥4.20 | ±0.21 |
| 16 | 37 | 6.05 | ±0.28 | ≤1.50 | ±0.00 | n.d. | ≥4.55 | ±0.28 |
| | | | | 0.10% | | | | |
| 16 | RT | 6.05 | ±0.26 | ≤2.50 | ±0.00 | n.d. | ≥3.55 | ±0.26 |
| 16 | 37 | 5.75 | ±0.22 | ≤2.50 | ±0.00 | n.d. | ≥3.25 | ±0.22 |

TABLE 6

Inactivation of Coxsackie-Virus A16 by 069-1

| | | TCID$_{50}$/ml | | TCID$_{50}$/ml after inactivation | | | | |
|---|---|---|---|---|---|---|---|---|
| | $T_{IA}$ | Hold Sample | | Titration | | Res. virus test | LRV | |
| $t_{IA}$ hours | ° C. | log 10 | 95% CI | log 10 | 95% CI | log 10 | log 10 | 95% CI |
| | | | | 0.05% | | | | |
| 16 | RT | 7.45 | ±0.33 | 7.55 | ±0.28 | n.d. | −0.10 | ±0.43 |
| 24 | 37 | 7.40 | ±0.28 | ≤2.40 | ±0.27 | n.d. | ≥5.00 | ±0.39 |
| 48 | 37 | 7.10 | ±0.29 | ≤1.50 | ±0.00 | n.d. | ≥5.60 | ±0.29 |

TABLE 6-continued

Inactivation of Coxsackie-Virus A16 by 069-1

| | | TCID$_{50}$/ml | | TCID$_{50}$/ml after inactivation | | | |
|---|---|---|---|---|---|---|---|
| | T$_{IA}$ | Hold Sample | | Titration | | Res. virus test | LRV |
| t$_{IA}$ hours | °C. | log 10 | 95% CI | log 10 | 95% CI | log 10 | log 10 95% CI |
| | | | | 0.10% | | | |
| 16 | RT | 7.40 | ±0.32 | 2.15 | ±0.30 | n.d. | 5.25 ±0.44 |
| 16 | 37 | 7.20 | ±0.28 | ≤1.50 | ±0.00 | n.d. | ≥5.70 ±0.28 |
| 16 | 37 | 7.40 | ±0.33 | 3.75 | ±0.24 | n.d. | 3.65 ±0.41 |

TABLE 7

Inactivation of Echovirus 6 by 069-1

| | | TCID$_{50}$/ml | | TCID$_{50}$/ml after inactivation | | | |
|---|---|---|---|---|---|---|---|
| | T$_{IA}$ | Hold Sample | | Titration | | Res. virus test | LRV |
| t$_{IA}$ hours | °C. | log 10 | 95% CI | log 10 | 95% CI | log 10 | log 10 95% CI |
| | | | | 0.05% | | | |
| 6 | 37 | 8.95 | ±0.26 | 8.00 | ±0.33 | n.d. | 0.95 ±0.42 |
| 16 | 6 | 8.90 | ±0.25 | 9.15 | ±0.25 | n.d. | −0.25 ±0.35 |
| 16 | RT | 9.10 | ±0.24 | 8.55 | ±0.31 | n.d. | 0.55 ±0.39 |
| 24 | RT | 8.45 | ±0.30 | 8.30 | ±0.27 | n.d. | 0.15 ±0.40 |
| 24 | 37 | 8.55 | ±0.34 | 6.55 | ±0.28 | n.d. | 2.00 ±0.44 |
| 48 | RT | 8.60 | ±0.28 | 7.20 | ±0.35 | n.d. | 1.40 ±0.45 |
| 48 | 37 | 8.30 | ±0.27 | 3.45 | ±0.30 | n.d. | 4.85 ±0.40 |
| | | | | 0.10% | | | |
| 6 | RT | 8.80 | ±0.27 | 8.05 | ±0.30 | n.d. | 0.75 ±0.40 |
| 6 | 37 | 8.90 | ±0.25 | 5.50 | ±0.29 | n.d. | 3.40 ±0.38 |
| 6 | 37 | 8.55 | ±0.32 | 5.70 | ±0.21 | n.d. | 2.85 ±0.38 |
| 16 | RT | 8.70 | ±0.18 | 7.05 | ±0.23 | n.d. | 1.65 ±0.29 |
| 16 | RT | 8.30 | ±0.25 | 7.10 | ±0.29 | n.d. | 1.20 ±0.39 |
| 16 | 37 | 8.50 | ±0.18 | 3.20 | ±0.30 | n.d. | 5.30 ±0.35 |
| 16 | 37 | 8.40 | ±0.28 | 3.10 | ±0.25 | n.d. | 5.30 ±0.38 |

TABLE 8

Inactivation of Herpes Simplex Virus 1 by 069-1

| | | TCID$_{50}$/ml | | TCID$_{50}$/ml after inactivation | | | |
|---|---|---|---|---|---|---|---|
| | T$_{IA}$ | Hold Sample | | Titration | | Res. virus test | LRV |
| t$_{IA}$ hours | °C. | log 10 | 95% CI | log 10 | 95% CI | log 10 | log 10 95% CI |
| | | | | 0.05% | | | |
| 6 | 37 | 8.55 | ±0.23 | 5.75 | ±0.33 | n.d. | 2.80 ±0.40 |
| 16 | RT | 8.55 | ±0.29 | 3.70 | ±0.28 | n.d. | 4.85 ±0.41 |
| 24 | RT | 8.60 | ±0.18 | ≤1.50 | ±0.00 | n.d. | ≥7.10 ±0.18 |
| 24 | RT | 8.35 | ±0.26 | ≤1.50 | ±0.00 | ≤−1.5 | ≥9.85 ±0.26 |
| 48 | RT | 8.45 | ±0.26 | 3.05* | ±0.30 | n.d. | 5.40* ±0.39 |
| 48 | RT | 8.15 | ±0.31 | 3.05* | ±0.27 | n.d. | 5.10* ±0.42 |
| | | | | 0.10% | | | |
| 6 | RT | 8.60 | ±0.25 | ≤1.50 | ±0.00 | n.d. | ≥7.10 ±0.25 |
| 6 | RT | 8.50 | ±0.00 | ≤1.50 | ±0.00 | ≤−1.5 | ≥10.00 ±0.00 |
| 6 | 37 | 8.35 | ±0.26 | ≤1.50 | ±0.00 | n.d. | ≥6.85 ±0.26 |
| 16 | RT | 8.50 | ±0.25 | ≤1.50 | ±0.00 | n.d. | ≥7.00 ±0.25 |
| 16 | 37 | 7.80 | ±0.23 | ≤1.50 | ±0.00 | n.d. | ≥6.30 ±0.23 |

*Results from 2 independent test runs.

TABLE 9

Inactivation of Parainfluenza virus type 3 by 069-1

| | | $TCID_{50}$/ml Hold Sample | | $TCID_{50}$/ml after inactivation Titration | | Res. virus test | LRV | |
|---|---|---|---|---|---|---|---|---|
| $t_{IA}$ hours | $T_{IA}$ °C. | log 10 | 95% CI | log 10 | 95% CI | log 10 | log 10 | 95% CI |
| 0.025% | | | | | | | | |
| 16 | RT | 7.55 | ±0.28 | 2.90 | ±0.24 | n.d. | 4.65 | ±0.37 |
| 16 | 37 | 6.90 | ±0.28 | ≤1.50 | ±0.00 | n.d. | ≥5.40 | ±0.28 |
| 0.05% | | | | | | | | |
| 16 | RT | 7.55 | ±0.31 | ≤1.50 | ±0.00 | n.d. | ≥6.05 | ±0.31 |
| 16 | RT | 7.35 | ±0.21 | ≤1.50 | ±0.00 | ≤−0.5 | ≥7.85 | ±0.21 |
| 16 | 37 | 7.55 | ±0.35 | ≤1.50 | ±0.00 | n.d. | ≥6.05 | ±0.35 |
| 16 | 37 | 7.00 | ±0.29 | ≤1.50 | ±0.00 | n.d. | ≥5.50 | ±0.29 |
| 0.10% | | | | | | | | |
| 16 | RT | 7.55 | ±0.31 | ≤2.50 | ±0.00 | n.d. | ≥5.05 | ±0.31 |
| 16 | 37 | 6.60 | ±0.35 | ≤2.50 | ±0.00 | n.d. | ≥4.10 | ±0.35 |

TABLE 10

Inactivation of Minute Virus of Mice Parvovirus by 069-1

| | | $TCID_{50}$/ml Hold Sample | | $TCID_{50}$/ml after inactivation Titration | | Res. virus test | LRV | |
|---|---|---|---|---|---|---|---|---|
| $t_{IA}$ hours | $T_{IA}$ °C. | log 10 | 95% CI | log 10 | 95% CI | log 10 | log 10 | 95% CI |
| 0.05% | | | | | | | | |
| 6 | 37 | 7.70 | ±0.21 | 4.40 | ±0.25 | n.d. | 3.30 | ±0.32 |
| 16 | 6 | 7.20 | ±0.32 | 4.70 | ±0.18 | n.d. | 2.50 | ±0.37 |
| 16 | RT | 7.45 | ±0.31 | 4.50 | ±0.29 | n.d. | 2.95 | ±0.43 |
| 24 | RT | 7.00 | ±0.28 | 5.15 | ±0.31 | n.d. | 1.85 | ±0.42 |
| 24 | 37 | 7.00 | ±0.29 | 4.35 | ±0.26 | n.d. | 2.65 | ±0.39 |
| 48 | RT | 6.95 | ±0.26 | 5.10 | ±0.34 | n.d. | 1.85 | ±0.43 |
| | 37 | 7.45 | ±0.28 | 3.65 | ±0.31 | n.d. | 3.80 | ±0.41 |
| 0.10% | | | | | | | | |
| 6 | RT | 7.55 | ±0.31 | 4.90 | ±0.25 | n.d. | 2.65 | ±0.40 |
| 6 | 37 | 7.50 | ±0.18 | 3.95 | ±0.26 | n.d. | 3.55 | ±0.32 |
| 16 | RT | 7.60 | ±0.24 | 3.50 | ±0.18 | n.d. | 4.10 | ±0.30 |
| 16 | RT | 7.05 | ±0.28 | 4.90 | ±0.25 | n.d. | 2.15 | ±0.38 |
| 16 | 37 | 6.75 | ±0.25 | 3.90 | ±0.25 | n.d. | 2.85 | ±0.35 |
| 16 | 37 | 7.65 | ±0.24 | 4.95 | ±0.26 | n.d. | 2.70 | ±0.36 |
| 24 | 37 | 7.60 | ±0.30 | 3.20 | ±0.28 | n.d. | 4.40 | ±0.42 |
| 48 | 37 | 7.35 | ±0.36 | ≤2.50 | ±0.00 | n.d. | ≥4.85 | ±0.36 |

TABLE 11

Inactivation of Reovirus 3 by 069-1

| | | $TCID_{50}$/ml Hold Sample | | $TCID_{50}$/ml after inactivation Titration | | Res. virus test | LRV | |
|---|---|---|---|---|---|---|---|---|
| $t_{IA}$ hours | $T_{IA}$ °C. | log 10 | 95% CI | log 10 | 95% CI | log 10 | log 10 | 95% CI |
| 0.025% | | | | | | | | |
| 16 | RT | 9.45 | ±0.13 | 3.50 | ±0.00 | n.d. | 5.95 | ±0.13 |
| 16 | 37 | 9.10 | ±0.25 | 2.65 | ±0.16 | n.d. | 6.45 | ±0.30 |

TABLE 11-continued

Inactivation of Reovirus 3 by 069-1

| | | TCID$_{50}$/ml Hold Sample | | TCID$_{50}$/ml after inactivation | | | LRV | |
|---|---|---|---|---|---|---|---|---|
| | T$_{IA}$ | | | Titration | | Res. virus test | | |
| t$_{IA}$ hours | °C. | log 10 | 95% CI | log 10 | 95% CI | log 10 | log 10 | 95% CI |
| | | | | 0.05% | | | | |
| 6 | RT | 9.30 | ±0.23 | 3.50 | ±0.00 | n.d. | 5.80 | ±0.23 |
| 6 | 37 | 9.40 | ±0.16 | 1.50 | ±0.00 | n.d. | ≥7.90 | ±0.16 |
| 16 | RT | 9.30 | ±0.23 | 1.50 | ±0.00 | ≤0.5 | ≥8.80 | ±0.23 |

TABLE 12

Inactivation of Rabies virus by 069-1

| | | TCID$_{50}$/ml Hold Sample | | TCID$_{50}$/ml after inactivation | | | LRV | |
|---|---|---|---|---|---|---|---|---|
| | T$_{IA}$ | | | Titration | | Res. virus test | | |
| t$_{IA}$ hours | °C. | log 10 | 95% CI | log 10 | 95% CI | log 10 | log 10 | 95% CI |
| | | | | 0.0125% | | | | |
| 18 | 2-8/37[#] | 8.3 | ±0.31 | 4.8 | ±0.31 | n.d. | 3.5 | ±0.31 |
| | | 8.4 | ±0.41 | 3.5 | ±0.00 | n.d. | 4.9 | ±0.41 |
| | | | | 0.025% | | | | |
| 18 | 2-8/37[#] | 8.3 | ±0.31 | ≤2.8 | ±0.00 | ≤0.5 | ≥5.5 | ±0.31 |
| | | 8.4 | ±0.41 | n.d. | | ≤0.5 | ≥7.9 | ±0.41 |
| | | | | 0.05 | | | | |
| 18 | 2-8/37[#] | 8.3 | ±0.31 | n.d. | ±0.31 | ≤0.5 | ≥7.8 | ±0.31 |
| | | 8.4 | ±0.41 | n.d. | ±0.31 | ≤0.5 | ≥7.9 | ±0.41 |

[#]: All inactivations were done for 16 hours at 2-8° C., then the inactivation temperature was raised to 37° C. for 2 hours.
Therafter the inactivation was stopped by addition of ascorbic acid.

TABLE 13

Inactivation of Influenza viruses by 069-1

| | | TCID$_{50}$/ml Hold Sample | | TCID$_{50}$/ml after inactivation | | | LRV | |
|---|---|---|---|---|---|---|---|---|
| | T$_{IA}$ | | | Titration | | Res. virus test | | |
| t$_{IA}$ hours | °C. | log 10 | 95% CI | log 10 | 95% CI | log 10 | log 10 | 95% CI |
| | | | | 0.05% | | | | |
| 8 | RT | 3.55 | n.d. | ≤2.5 | n.d | ≤−1.5 | ≥5.05 | n.d. |
| 8 | RT | 6.05 | n.d. | ≤2.5 | n.d. | ≤−1.5 | ≥7.55 | n.d. |
| 8 | RT | 5.2 | n.d. | ≤2.5 | n.d. | ≤−1.5 | ≥6.7 | n.d. |
| 16 | 2-8 | 6.6 | n.d. | ≤2.5 | n.d | ≤−1.5 | ≥8.1 | n.d. |
| 16 | 2-8 | 4.7 | n.d. | ≤2.5 | n.d. | ≤−1.5 | ≥6.2 | n.d. |
| 16 | 2-8 | 6.55 | n.d. | ≤2.5 | n.d. | ≤−1.5 | ≥5.05 | n.d. |
| 16 | 2-8 | 6.5 | n.d. | ≤2.5 | n.d. | ≤−1.5 | ≥8.0 | n.d. |
| 16 | 2-8 | 6.4 | n.d. | ≤2.5 | n.d. | ≤−1.5 | ≥7.9 | n.d. |
| 16 | 2-8 | 3.55 | n.d. | ≤2.5 | n.d | ≤−1.5 | ≥5.05 | n.d. |
| 16 | 2-8 | 6.05 | n.d. | ≤2.5 | n.d. | ≤−1.5 | ≥7.55 | n.d. |
| 16 | 2-8 | 5.2 | n.d. | ≤2.5 | n.d. | ≤−1.5 | ≥6.7 | n.d. |
| | | | | 0.1% | | | | |
| 3 | RT | 6.05 | n.d. | ≤2.5 | n.d. | ≤−1.5 | ≥7.55 | n.d. |
| 3 | RT | 5.2 | n.d. | ≤2.5 | n.d. | ≤−1.5 | ≥6.7 | n.d. |
| 3 | RT | 3.7 | n.d. | ≤2.5 | n.d. | ≤−1.5 | ≥5.2 | n.d. |

TABLE 13-continued

Inactivation of Influenza viruses by 069-1

| | | TCID$_{50}$/ml | | TCID$_{50}$/ml after inactivation | | | LRV | |
|---|---|---|---|---|---|---|---|---|
| | T$_{IA}$ | Hold Sample | | Titration | | Res. virus test | | |
| t$_{IA}$ hours | °C. | log 10 | 95% CI | log 10 | 95% CI | log 10 | log 10 | 95% CI |
| 6 | RT | 6.05 | n.d. | ≤2.5 | n.d. | ≤−1.5 | ≥7.55 | n.d. |
| 6 | RT | 5.2 | n.d. | ≤2.5 | n.d. | ≤−1.5 | ≥6.7 | n.d. |
| 6 | RT | 3.7 | n.d. | ≤2.5 | n.d. | ≤−1.5 | ≥5.3 | n.d. |

Strain differences were not observed, thus the individual strains (see 3 above) were not indicated in this table.

TABLE 14

Comparative data for inactivation with BPL

| DNA/RNA Type | ENV | Virus Type | Inactivation agent/conditions | LRV |
|---|---|---|---|---|
| double-stranded DNA | − | BK Polyoma virus | BPL 0.05%; 16 hours +2-8° C. (then 2 hours 37° C. for BPL hydrolysis) | 2.1 |
| single-stranded RNA | − | Enteroviruses (Coxsackie virus, Echovirus) | | 4-5 |
| single-stranded RNA | + | Paramyxovirus, Parainfluenzavirus 3 | | ≥9.5 (complete inactivation) |

Abbreviations Used in the Tables:
  t$_{IA}$: Inactivation time/duration in hours
  T$_{IA}$: Inactivation temperature
  TCID$_{50}$/ml: 50% tissue culture infectious units per mL
  LRV: Log 10 reduction value
  Res. virus test: Test for residual virus using larger sample volumes (see also text above)
  95% CI: 95% confidence interval
  RT: ambient (room) temperature, which was in a range of 17-26° C.
  n.d.: not done or not determined
  % value indicate the end concentration of the inactivating agent.

DNA Damage Tables

TABLE 15

Abasic sites induced by inactivation

| Inactivator | Concentration (%) | Temperature (° C.) | Relative number of APS |
|---|---|---|---|
| Influenza A/Christchurch//16/10 infected cell DNA | | | |
| None | | 2-8 | 1 |
| BPL | 0.05 | 2-8/37 | 0.6 |
| 069-1 | 0.025 | 2-8 | 15 |
| 069-1 | 0.025 | 37 | 26 |
| 069-1 | 0.05 | 2-8 | 6 |
| 069-1 | 0.05 | 37 | 46 |
| 069-1 | 0.1 | 2-8 | 50 |
| 069-1 | 0.1 | 37 | 66 |
| Influenza A/Brisbane/10/2010 infected cell DNA | | | |
| None | | 2-8 | 1 |
| BPL | 0.05 | 2-8/37 | 29 |
| 069-1 | 0.025 | 2-8 | 42 |
| 069-1 | 0.025 | 37 | 67 |
| 069-1 | 0.05 | 2-8 | 48 |

TABLE 15-continued

Abasic sites induced by inactivation

| Inactivator | Concentration (%) | Temperature (° C.) | Relative number of APS |
|---|---|---|---|
| 069-1 | 0.05 | 37 | 119 |
| 069-1 | 0.1 | 2-8 | 109 |
| 069-1 | 0.1 | 37 | 146 |
| Influenza A/California/7/09 infected cell DNA | | | |
| None | | 2-8 | 1 |
| BPL | 0.05 | 4/37 | 63 |
| 069-1 | 0.025 | 2-8 | 25 |
| 069-1 | 0.025 | 37 | 50 |
| 069-1 | 0.05 | 2-8 | 16 |
| 069-1 | 0.05 | 37 | 23 |
| 069-1 | 0.1 | 2-8 | 63 |
| 069-1 | 0.1 | 37 | 89 |

TABLE 16

Abasic sites induced by single/double inactivation with different concentrations of 069-1

| | Inactivator | Concentration (%) | Temperature (° C.) | Relative number of APS |
|---|---|---|---|---|
| Influenza B/Wisconsin/1/2010 infected cell DNA | | | | |
| single inactivation treatment | None | | 2-8 | 1 |
| | BPL | 0.05 | 2-8/37 | 30 |
| | 069-1 | 0.025 | 2-8 | 39 |
| | 069-1 | 0.025 | 37 | 43 |
| | 069-1 | 0.05 | 2-8 | 39 |
| | 069-1 | 0.05 | 37 | 58 |

TABLE 16-continued

Abasic sites induced by single/double inactivation
with different concentrations of 069-1

| Inactivator | | Concentration (%) | Temperature (° C.) | Relative number of APS |
|---|---|---|---|---|
| | 069-1 | 0.1 | 2-8 | 56 |
| | 069-1 | 0.1 | 37 | 53 |
| twofold | 069-1 | 0.025 | 2-8 | 69 |
| inactivation | 069-1 | 0.025 | 37 | 88 |
| treatment | 069-1 | 0.05 | 2-8 | 57 |
| | 069-1 | 0.05 | 37 | 94 |
| | 069-1 | 0.1 | 2-8 | 85 |
| | 069-1 | 0.1 | 37 | 73 |

TABLE 17

Abasic sites induced by double inactivation with BPL and 069-1

| Inaktivator | | Concentration (%) | Temperature (° C.) | Relative number of APS |
|---|---|---|---|---|
| Influenza B/Wisconsin/1/2010 infected cell DNA | | | | |
| Single | None | | 2-8 | 1 |
| inactivation | BPL | 0.05 | 2-8/37 | 2 |
| treatment | 069-1 | 0.05 | 2-8/37 | 10 |
| | 069-1 | 0.025 | 2-8 | 5 |
| | 069-1 | 0.025 | 37 | 3 |
| | 069-1 | 0.05 | 2-8 | 8 |
| | 069-1 | 0.05 | 37 | 8 |
| | 069-1 | 0.1 | 2-8 | 15 |
| | 069-1 | 0.1 | 37 | 15 |
| Twofold | BPL | 0.05 | 2-8/37 | 20 |
| inactivation | 069-1 | 0.05 | 2-8/37 | 93 |
| treatment: | 069-1 | 0.025 | 2-8 | 79 |
| BPL plus | 069-1 | 0.025 | 37 | 141 |
| BPL or 069- | 069-1 | 0.05 | 2-8 | 150 |
| 1 | 069-1 | 0.5 | 37 | 172 |
| | 069-1 | 0.1 | 2-8 | 205 |
| | 069-1 | 0.1 | 37 | 110 |

The twofold inactivation samples were diluted since without dilution all values were far above the test range. For comparison the dilution factor was used to calculate the relative APS numbers given in this table.

Inactivators Useful with the Invention (See Also FIG. 1)

For comparison, the following mono-functional organic peroxide was also tested:

| 072 | Methylhydroperoxide, $CH_3$—OOH |

REFERENCES

[1] *Handbuch der Schutzimpfungen in der Tiermedizin* (eds. Mayr et al.). Verlad Paul Barey, 1984.
[2] WO2007/052163.
[3] European guidelines on Viral Safety Evaluations of Biotechnology Products; ICH Q5A (CPMP/ICH/295/95).
[4] Note for Guidance on the use of bovine serum in the manufacture of human biological medicinal products, CPMP/BWP/1793/02.
[5] Moghaddam et al. (2006) *Nature Medicine* 12:905-7.
[6] Haas et al. (1959) *Arch Gesamte Virusforsch.* 9:470-83.
[7] Rheinbaben & Wolff; *Handbuch der viruswirksamen Desinfektionen*; Springer 2002; p 163.
[8] Hamann et al. (2008) *Chem Eur J* 14:6849-51.
[9] Bunge et al. (2009) *Tetrahedron letters* 50:524-6
[10] Žmitek et al. (2007) *Org Biomol Chem* 5:3895-908.
[11] Kistner et al. (1998) *Vaccine* 16:960-8.
[12] Kistner et al. (1999) *Dev Biol Stand* 98:101-10.
[13] Bruhl et al. (2000) *Vaccine* 19:1149-58.
[14] WO97/37000.
[15] Brands et al. (1999) *Dev Biol Stand* 98:93-100.
[16] Halperin et al. (2002) *Vaccine* 20:1240-7.
[17] Tree et al. (2001) *Vaccine* 19:3444-50.
[18] Kistner et al. (1998) *Vaccine* 16:960-8.
[19] Kistner et al. (1999) *Dev Biol Stand* 98:101-110.
[20] Bruhl et al. (2000) *Vaccine* 19:1149-58.
[21] Pau et al., (2001) *Vaccine* 19:2716-21.
[22] http://www.atcc.org/
[23] http://locus.umdnj.edu/
[24] WO03/076601.
[25] WO2005/042728.
[26] WO03/043415.
[27] WO01/85938.
[28] WO2006/108846.
[29] WO97/37000.
[30] Brands et al. (1999) *Dev Biol Stand* 98:93-100.

TABLE 18

| Code | Details |
|---|---|
| 054 | 1,1-Dihydroperoxymethane |
| 056-1 | (dimer) $C_8H_{18}O_6$ 2,2'-Dihydroperoxy-2,2'-dibutylperoxide |
| 058-1 | $C_4H_{10}O_4$ 2,2-Dihydroperoxybutane |
| 057-1 | mixture of 056-1 and 058-1 (1:1 ratio) |
| 069-1 | $C_2H_6O_4$ 1,1-Dihydroperoxyethane<br>Hydroperoxide-1,1'-ethylidenebis<br>Also known as ethane-1,1-dihydroperoxide [8] or 1,1-bishydroperoxyethane. |
| 070-1 | $C_3H_8O_4$ 1,1 -Dihydroperoxypropane |
| 071-1 | $C_4H_{14}O_4$ 1,1-Dihydroperoxybutane |
| 077 | (dimer) $C_6H_{14}O_6$ 1,1-Dihydroperoxypropane + 1,1'-Dihydroperoxy-1,1'-dipropylperoxide |
| 078 | (dimer) $C_8H_{18}O_6$ 1,1-Dihydroperoxybutane + 1,1'-Dihydroperoxy-1,1'-dibutylperoxide |
| 079 | $C_4H_8O_4$ 1,1-Dihydroperoxyethane + 1,1'-Dihydroperoxy-1,1'-diethylperoxide |
| 080 | $C_5H_4O_8$ and/or with closed ring $C_5H_2O_6$ 1,1,5,5-Tetrahydroperoxypentane + 3,7-Bishydroperoxy-1,2-dioxepane |

[31] Halperin et al. (2002) Vaccine 20:1240-7.
[32] EP-A-1260581 (WO01/64846).
[33] WO2006/071563.
[34] WO2005/113758.
[35] WO03/023021
[36] WO03/023025
[37] *Remington: The Science and Practice of Pharmacy* (Gennaro, 2000; 20th edition, ISBN: 0683306472)
[38] *Vaccine Design: The Subunit and Adjuvant Approach* (eds. Powell & Newman) Plenum Press 1995 (ISBN 0-306-44867-X).
[39] *Vaccine Adjuvants: Preparation Methods and Research Protocols* (Volume 42 of *Methods in Molecular Medicine* series). ISBN: 1-59259-083-7. Ed. O'Hagan.
[40] *Vaccine Design: The Subunit and Adjuvant Approach* (eds. Powell & Newman) Plenum Press 1995 (ISBN 0-306-44867-X).
[41] Lundblad (2001) *Biotechnology and Applied Biochemistry* 34:195-197.
[42] *Guidance for Industry: Bioanalytical Method Validation*. U.S. Department of Health and Human Services Food and Drug Administration Center for Drug Evaluation and Research (CDER) Center for Veterinary Medicine (CVM). May 2001.
[43] Ji et al, (2002) *Biotechniques*. 32:1162-7.
[44] Briggs (1991) *J Parenter Sci Technol*. 45:7-12.
[45] Lahijani et al. (1998) *Hum Gene Ther*. 9:1173-80.
[46] Lokteff et al. (2001) *Biologicals*. 29:123-32.
[47] WO02/28422
[48] WO02/067983
[49] WO02/074336
[50] WO01/21151
[51] WO02/097072
[52] WO2005/113756
[53] Treanor et al. (1996) *J Infect Dis* 173:1467-70
[54] Keitel et al. (1996) *Clin Diagn Lab Immunol* 3:507-10
[55] WO2008/068631
[56] Spaulding. *Chemical disinfection of medical and surgical materials*. In: Block (Editor): *Disinfection, Sterilization, and Preservation*. Chapter 32, pages 517-31. Lippincott Williams & Wilkins, 1968.
[57] Darling et al. (1998) *Biologicals* 26:105-10.
[58] Favero & Bond. *Chemical disinfection of medical and surgical materials*. In: Block (Editor): *Disinfection, Sterilization, and Preservation*. Chapter 35, pages 617-41. Lea and Febinger, 1991.
[59] ICH Q5A. Viral safety evaluation of biotechnology products derived from cell lines of human or animal origin. 1999.

-continued
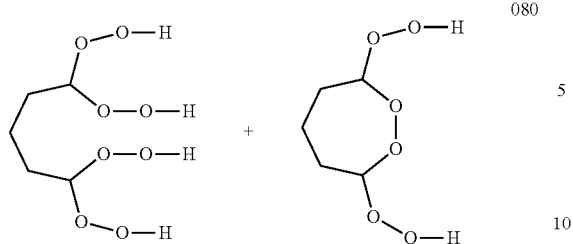
or a combination thereof.
35. The method of claim 1, wherein the multifunctional organic peroxide is a compound of the formula:
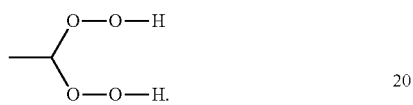

The invention claimed is:

1. A method for preparing a pharmaceutical composition, comprising steps of: (i) contacting a microorganism-containing sample with a multifunctional organic peroxide to inactivate microorganisms therein; and (ii) preparing a pharmaceutical composition from the product of step (i), wherein the multifunctional organic peroxide has a structure of one of the compounds of the following formula:

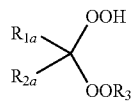

(I)

where:
$R_{1a}$ is H;
$R_{2a}$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$alkyl, amino, N-mono or N-di $C_{1-6}$alkylated amino, aminocarbonyl, N-mono or N-di $C_{1-6}$alkylated aminocarbonyl, S(O)$_{0-2}C_{1-6}$alkyl, heterocycloalkyl, aryl or heteroaryl, —(CR$_4$R$_5$)$_n$CR$_6$(OOH)$_2$;
$R_3$ is H or C(OOH)R$_{1b}$R$_{2b}$,
$R_{1b}$ is H, $C_{1-6}$alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$alkyl, amino, N-mono or N-di $C_{1-6}$alkylated amino, aminocarbonyl, N-mono or N-di $C_{1-6}$alkylated aminocarbonyl, S(O)$_{0-2}C_{1-6}$alkyl, heterocycloalkyl, aryl or heteroaryl,
$R_{2b}$ is H, $C_{1-6}$ alkyl, $C_{2-6}$alkenyl, $C_{1-6}$alkynyl, $C_{1-6}$-alkoxy, $C_{2-6}$-alkenyloxy, C(O)H, C(O)$C_{1-6}$alkyl, C(O)O$C_{1-6}$alkyl amino, N-mono or N-di $C_{1-6}$alkylated amino, aminocarbonyl, N-mono or N-di $C_{1-6}$alkylated aminocarbonyl, S(O)$_{0-2}C_{1-6}$alkyl, heterocycloalkyl, aryl or heteroaryl, or
$R_{2b}$ is linked to $R_{2a}$ by L, wherein L is $C_{1-8}$alkylene;
$R_4$ is, at each occurrence, selected from H or $C_{1-3}$ alkyl, hydroxyl, cyano, nitro, $C_{2-4}$-alkenyl, $C_{1-3}$-alkoxy, $C_{2-4}$-alkenyloxy, $C_{1-3}$-alkylcarbonyl, carboxy, $C_{1-6}$-alkoxycarbonyl, aminocarbonyl, N-mono or N-di $C_{1-3}$alkylated aminocarbonyl, $C_{1-3}$-thioalkyl, $C_{1-3}$-alkylsulfinyl, $C_{1-3}$-alkylsulfonyl, $C_{1-3}$-alkylaminosulfonyl and di-$C_{1-3}$-alkylaminosulfonyl;
$R_5$ is, at each occurrence, selected from H or $C_{1-3}$ alkyl, hydroxyl, cyano, nitro, $C_{2-4}$-alkenyl, $C_{1-3}$-alkoxy, $C_{2-4}$-alkenyloxy, $C_{1-3}$-alkylcarbonyl, carboxy, $C_{1-6}$-alkoxycarbonyl, aminocarbonyl, N-mono or N-di $C_{1-3}$alkylated aminocarbonyl, $C_{1-3}$-thioalkyl, $C_{1-3}$-alkylsulfinyl, $C_{1-3}$-alkylsulfonyl, $C_{1-3}$-alkylaminosulfonyl and di-$C_{1-3}$-alkylaminosulfonyl; $R_6$ is H $C_{1-6}$alkyl, $C_{2-6}$alkenyl, $C_{1-6}$-alkoxy, $C_{2-6}$-alkenyloxy, C(O)H, C(O)$C_{1-6}$alkyl, C(O)O$C_{1-6}$alkyl, amino, N-mono or N-di $C_{1-6}$alkylated amino, aminocarbonyl, N-mono or N-di $C_{1-6}$alkylated aminocarbonyl, S(O)$_{0-2}C_{1-6}$alkyl, heterocycloalkyl, aryl or heteroaryl;
n is 1 to 8; and
wherein the immunogenicity of the microorganisms is not reduced.

2. The method of claim 1, wherein the sample is from the surface of a container or the surface of a workplace.

3. The method of claim 1, wherein the microorganism-containing sample also includes nucleic acid in solution.

4. The method of claim 1, wherein the sample is obtained from a cell culture and the nucleic acids are cellular DNA from the cell culture.

5. The method of claim 1, wherein the sample contains a virus.

6. The method of claim 5, wherein the sample contains a non-enveloped DNA virus.

7. The method of claim 1, wherein the multifunctional organic peroxide is a geminal peroxide.

8. The method of claim 1, wherein the multifunctional organic peroxide has two, three or four peroxide groups.

9. The method of claim 1, wherein the multifunctional organic peroxide is a geminal bishydroperoxide.

10. The method of claim 1, wherein the multifunctional organic peroxide is homobifunctional.

11. The method of claim 1, wherein the multifunctional organic peroxide is water-soluble.

12. The method of claim 1, wherein the multifunctional organic peroxide has a molecular weight below 300.

13. The method of claim 1, the multifunctional organic peroxide has formula II:

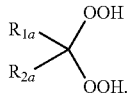

14. The method of claim 13, wherein: $R_{1a}$ is H; and $R_{2a}$ is $CH_3$, Et, or n-Pr.

15. The method of claim 1, where the multifunctional organic peroxide has formula III:

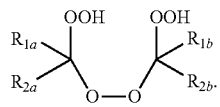

16. The method of claim 15, wherein: $R_{1a}$ is H; $R_{2a}$ is $CH_3$, Et, or n-Pr; $R_{1b}$ is H; $R_{2b}$ is $CH_3$, Et, or n-Pr, or $R_{2b}$ is linked to $R_{2a}$ by L; and L is —$(CH_2)_3$—.

17. The method of claim 1, where the multifunctional organic peroxide has formula IV:

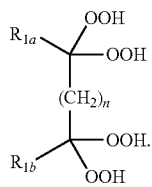

18. The method of claim 17, wherein: $R_{1a}$ is H; $R_{1b}$ is H; and n is 3.

19. The method of claim 1, where:
$R_{1a}$ and $R_{2a}$ are identical; and/or
$R_{1a}$ and $R_{2b}$ are identical; and/or
$R_{2a}$ and $R_{2b}$ are identical.

20. The method of claim where 1, where:
$R_{2a}$ is H or $C_{1-4}$alkyl or —$(CH_2)_nCH(OOH)_2$ or is linked to $R_{2b}$ by L; and/or
$R_{1b}$ is H or $C_{1-4}$alkyl; and/or
$R_{2b}$ is $C_{1-4}$alkyl or is linked to $R_{2a}$ by L; $R_{2b}$ can thus be $CH_3$, Et, or n-Pr; and/or
each $R_4$ is H or $CH_3$; and/or
each $R_5$ is H or $CH_3$; and/or
L is $C_{2-5}$alkylene; and/or
$R_6$ is H or $C_{1-4}$alkyl; and/or
n is 2 to 6.

21. The method of claim 1, wherein: $R_{2a}$ is $CH_3$, Et, n-Pr, or —$(CH_2)_nCH(OOH)_2$; $R_3$ is H or $C(OOH)R_{1b}R_{2b}$; $R_{1b}$ is H or $CH_3$; $R_{2b}$ is $CH_3$, Et, or n-Pr, or $R_{2b}$ is linked to $R_{2a}$ by L; L is —$(CH_2)_3$—; and n is 3.

22. The method of claim 1, wherein the multifunctional organic peroxide is selected from the group consisting of: 2,2'-Dihydroperoxy-2,2'-dibutylperoxide; 2,2-Dihydroperoxybutane; 1,1-1,2-dioxepane; and 1,1-dihydroperoxyethane.

23. The method of claim 1, wherein the multifunctional organic peroxide is used at a concentration between 0.01-0.25%.

24. The method of claim 1, wherein the multifunctional organic peroxide is used at a temperature between 0-50° C.

25. The method of claim 1, wherein the multifunctional organic peroxide is used for between 0.25-72 hours for inactivation.

26. The method of claim 1, wherein remaining or excess peroxide is removed after treatment of the sample.

27. The method of claim 26, wherein removal uses a reducing agent.

28. The method of claim 27, wherein the reducing agent is ascorbic acid or a reducing sugar.

29. The method of claim 1, wherein the pharmaceutical composition is a vaccine.

30. The method of claim 29, wherein the vaccine is a vetinary vaccine.

31. The method of claim 1, wherein the microorganism is present as a contaminant.

32. The method of claim 1, wherein the sample contains a virus propagated in a primary cell culture.

33. The method of claim 5, wherein the sample contains an influenza A virus, an influenza B virus, an influenza C virus, or a rabies virus.

34. The method of claim 1, wherein the multifunctional organic peroxide is a compound or mixture of compounds selected from the following formulas:

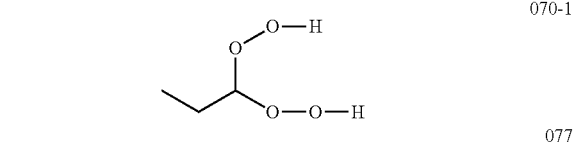
070-1

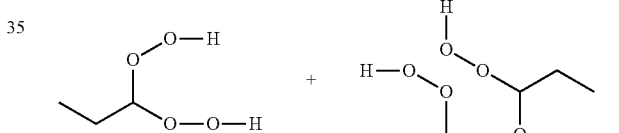
077

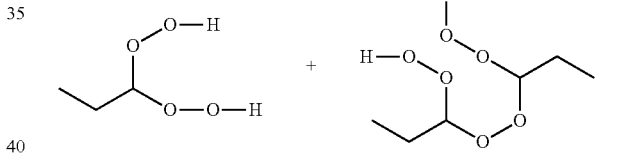
071-1

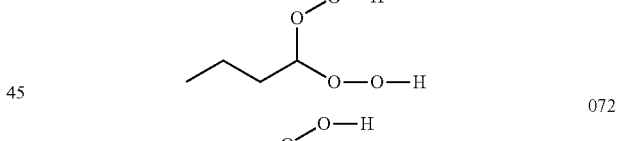
072

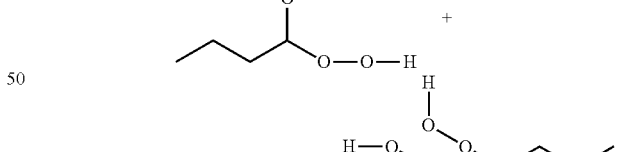
069-1

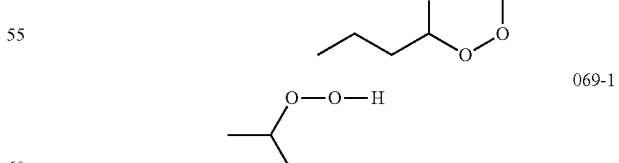
078